(12) United States Patent
Hiroi et al.

(10) Patent No.: US 11,470,841 B2
(45) Date of Patent: *Oct. 18, 2022

(54) CRYOPRESERVATION VESSEL

(71) Applicant: NISSAN CHEMICAL CORPORATION, Tokyo (JP)

(72) Inventors: Yoshiomi Hiroi, Funabashi (JP); Hiroyuki Nakajima, Shiraoka (JP); Taito Nishino, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 928 days.

This patent is subject to a terminal disclaimer.

(21) Appl. No.: 16/310,325

(22) PCT Filed: Jun. 9, 2017

(86) PCT No.: PCT/JP2017/021508
§ 371 (c)(1),
(2) Date: Mar. 28, 2019

(87) PCT Pub. No.: WO2017/217336
PCT Pub. Date: Dec. 21, 2017

(65) Prior Publication Data
US 2019/0327959 A1     Oct. 31, 2019

(30) Foreign Application Priority Data

Jun. 15, 2016   (JP) .............................. JP2016-118976

(51) Int. Cl.
*A01N 1/02*      (2006.01)
*C09D 143/02*    (2006.01)
*C08F 220/34*    (2006.01)

(52) U.S. Cl.
CPC .......... *A01N 1/0268* (2013.01); *C08F 220/34* (2013.01); *C09D 143/02* (2013.01)

(58) Field of Classification Search
CPC .... C08F 230/02; C08F 220/34; A01N 1/0268; C09D 185/02; C09D 201/00;
(Continued)

(56) References Cited

U.S. PATENT DOCUMENTS 5,178,963 A * 1/1993 Faust ..................... B41N 3/036
                                                        428/463
5,643,561 A    7/1997 Katsuen et al.
(Continued)

FOREIGN PATENT DOCUMENTS

CA      2914616 A1 * 12/2014 ............ C08F 230/02
CN     105307698 A      2/2016
(Continued)

OTHER PUBLICATIONS

Japanese Patent Office, International Search Report in International Patent Application No. PCT/JP2017/021508 (dated Sep. 12, 2017).
(Continued)

*Primary Examiner* — Lee E Sanderson
(74) *Attorney, Agent, or Firm* — Leydig, Voit & Mayer, Ltd.

(57) ABSTRACT

An object of the present invention is to provide a cryopreservation vessel which has a coating that is capable of inhibiting the adhesion of cells or proteins and is resistant not only to aqueous solvents but also to organic solvents (for example, cryoprotectants, in particular, dimethyl sulfoxide). The invention provides a cell or protein cryopreservation vessel including, on at least a portion of the surface thereof, a coating that includes a repeating unit containing a group represented by the following formula (a), and a repeating unit containing a group represented by the following formula (b) (wherein $U^{a1}$, $U^{a2}$, $U^{a3}$, $U^{b1}$, $U^{b2}$, $U^{b3}$ and $An^-$ are as defined in the description and the claims).

6 Claims, 4 Drawing Sheets

(58) Field of Classification Search
CPC ....... C09D 143/02; A61L 27/00; A61L 31/14; C12M 3/00; B05D 3/06
USPC .......................................... 424/78.08–78.38
See application file for complete search history.

(56) References Cited

U.S. PATENT DOCUMENTS

| | | | |
|---|---|---|---|
| 5,648,442 | A | 7/1997 | Bowers et al. |
| 10,774,165 | B2 | 9/2020 | Hyuugaji |
| 10,774,234 | B2 | 9/2020 | Otani et al. |
| 10,889,791 | B2 | 1/2021 | Katayama et al. |
| 2008/0045686 | A1 | 2/2008 | Meagher et al. |
| 2008/0063572 | A1 | 3/2008 | Deutsch et al. |
| 2008/0081369 | A1 | 4/2008 | Adkisson, IV et al. |
| 2010/0028286 | A1 | 2/2010 | Carballada et al. |
| 2010/0096327 | A1 | 4/2010 | Gin et al. |
| 2012/0214230 | A1 | 8/2012 | Anneren et al. |
| 2014/0147879 | A1 | 5/2014 | Wakamoto et al. |
| 2014/0186945 | A1* | 7/2014 | Bradley ............... C12N 5/0606 435/352 |
| 2015/0017221 | A1* | 1/2015 | Hayashi ................ C08F 212/08 424/423 |
| 2016/0032238 | A1 | 2/2016 | Lawin et al. |
| 2016/0115435 | A1 | 4/2016 | Otani et al. |
| 2016/0122576 | A1 | 5/2016 | Hiroi et al. |
| 2016/0129176 | A1 | 5/2016 | Kanaki et al. |
| 2016/0168294 | A1 | 6/2016 | Hayashi et al. |
| 2017/0101497 | A1 | 4/2017 | Koguchi et al. |
| 2017/0107470 | A1 | 4/2017 | Fang-Yen |
| 2017/0267960 | A1 | 9/2017 | Tsukada et al. |
| 2017/0335266 | A1 | 11/2017 | Noda et al. |
| 2017/0349777 | A1 | 12/2017 | Hiroi et al. |
| 2018/0223024 | A1 | 8/2018 | Hyuugaji |
| 2018/0305652 | A1 | 10/2018 | Katayama et al. |
| 2019/0218413 | A1 | 7/2019 | Hiroi et al. |
| 2019/0233792 | A1 | 8/2019 | Hiroi et al. |
| 2020/0291339 | A1 | 9/2020 | Hiroi et al. |
| 2020/0369999 | A1 | 11/2020 | Suzuki et al. |
| 2021/0171890 | A1 | 6/2021 | Nakajima et al. |
| 2022/0026440 | A1 | 1/2022 | Otsuka et al. |

FOREIGN PATENT DOCUMENTS

| | | |
|---|---|---|
| EP | 1152242 A | 11/2001 |
| EP | 2878664 A1 | 6/2015 |
| EP | 3098299 A1 | 11/2016 |
| EP | 3318585 A1 | 5/2018 |
| EP | 3467095 A1 | 4/2019 |
| GB | 1110042.7 | 6/2011 |
| JP | H04-117276 A | 4/1992 |
| JP | H05-156204 A | 6/1993 |
| JP | H05-292957 A | 11/1993 |
| JP | H08-140673 A | 6/1996 |
| JP | H11-166015 A | 6/1999 |
| JP | 2002-005887 A | 1/2002 |
| JP | 2003-040937 A | 2/2003 |
| JP | 2006-084393 A | 3/2006 |
| JP | 2006-158961 A | 6/2006 |
| JP | 2007-063459 A | 3/2007 |
| JP | 2007-124982 A | 5/2007 |
| JP | 2007-326920 A | 12/2007 |
| JP | 2008-061609 A | 3/2008 |
| JP | 2008-191067 A | 8/2008 |
| JP | 2009-031121 A | 2/2009 |
| JP | 2010-236955 A | 10/2010 |
| JP | 2011-078316 A | 4/2011 |
| JP | 2012-512637 A | 6/2012 |
| JP | 2014-502610 A | 2/2014 |
| JP | 2014-120410 A | 6/2014 |
| JP | 2014-155471 A | 8/2014 |
| JP | 2015-226497 A | 12/2015 |
| JP | 2016-059690 A | 4/2016 |
| JP | 2017-060498 A | 3/2017 |
| JP | 2018-169349 A | 11/2018 |
| NL | 7603497 A | 10/1977 |
| WO | WO 2000/039582 A1 | 7/2000 |
| WO | WO 2010/079058 A2 | 7/2010 |
| WO | WO 2011/049524 A1 | 4/2011 |
| WO | WO 2011/098365 A1 | 8/2011 |
| WO | WO 2012/089337 A1 | 7/2012 |
| WO | WO 2012/172291 A1 | 12/2012 |
| WO | WO 2013/099901 A1 | 7/2013 |
| WO | WO 2013/144372 A1 | 10/2013 |
| WO | WO 2014/017513 A1 | 1/2014 |
| WO | WO 2014/196650 A1 | 12/2014 |
| WO | WO 2014/196652 A1 | 12/2014 |
| WO | WO 2015/178413 A1 | 11/2015 |
| WO | WO 2016/072369 A1 | 5/2016 |
| WO | WO 2016/093293 A1 | 6/2016 |
| WO | WO 2017/006850 A1 | 1/2017 |
| WO | WO 2017/022815 A1 | 2/2017 |
| WO | WO 2017/065279 A1 | 4/2017 |
| WO | WO 2017/204201 A1 | 11/2017 |
| WO | WO 2018/016463 A1 | 1/2018 |
| WO | WO 2019/065714 A1 | 4/2019 |
| WO | WO 2019/093442 A1 | 5/2019 |
| WO | WO 2019/107503 A1 | 6/2019 |
| WO | WO 2019/176515 A1 | 9/2019 |
| WO | WO 2020/100957 A1 | 5/2020 |

OTHER PUBLICATIONS

European Patent Office, Supplementary European Search Report in European Patent Application No. 17813233.8 (dated Apr. 9, 2019).
European Patent Office, Communication Pursuant to Article 94(3) EPC in European Patent Application No. 17813233.8 (dated Apr. 24, 2019).
dictionary.com, "Varnish," Dictionary Entry (2020).
Liaw et al., "Polymerization and application of 2-methacryloyloxyethyl phenyl phosphate in coatings," *Die Angewandte Makromolekulare Chemie*, 214(3750): 169-178 (1994).
Todaro et al., "Colon Cancer Stem Cells Dictate Tumor Growth and Resist Cell Death by Production of Interleukin-4," *Cell Stem Cell*, 1(4): 389-402 (2007).
China National Intellectual Property Office, The First Office Action in Chinese Patent Application No. 201680059049.1 (dated Dec. 27, 2019).
European Patent Office, Supplementary European Search Report in European Patent Application No. 16855532.4 (dated Sep. 28, 2018).
European Patent Office, Communication Pursuant to Article 94(3) EPC in European Patent Application No. 14808411.4 (dated Mar. 22, 2018).
European Patent Office, Communication Pursuant to Article 94(3) EPC in European Patent Application No. 16855532.4 (dated Oct. 11, 2018).
European Patent Office, Extended European Search Report in European Patent Application No. 18861999.3 (dated Oct. 15, 2020).
European Patent Office, Extended European Search Report in European Patent Application No. 18876536.6 (dated Dec. 11, 2020).
Japanese Patent Office, International Search Report in International Patent Application No. PCT/JP2014/065250 (dated Aug. 19, 2014).
Japanese Patent Office, International Search Report in International Patent Application No. PCT/JP2016/080547 (dated Nov. 22, 2016).
Japanese Patent Office, International Search Report in International Patent Application No. PCT/JP2017/019147 (dated Aug. 15, 2017).
Japanese Patent Office, International Search Report in International Patent Application No. PCT/JP2018/035641 (dated Dec. 18, 2018).
Japanese Patent Office, International Search Report in International Patent Application No. PCT/JP2018/041556 (dated Jan. 29, 2019).
Japanese Patent Office, International Search Report in International Patent Application No. PCT/JP2018/044014 (dated Feb. 26, 2019).
Japanese Patent Office, International Search Report in International Patent Application No. PCT/JP2019/044605 (dated Feb. 10, 2020).
Japanese Patent Office, Notification of Reasons for Refusal in Japanese Patent Application No. 2015-521514 (dated Mar. 13, 2018).
European Patent Office, European Search Report in European Patent Application 19883598.5 (dated Jun. 2, 2022).

(56) References Cited

OTHER PUBLICATIONS

European Patent Office, Communication Pursuant to Article 94(3) EPC in European Patent Application 19883598.5 (dated Jun. 14, 2022).
U.S. Appl. No. 14/896,639, filed Dec. 7, 2015.
U.S. Appl. No. 15/768,427, filed Apr. 13, 2018.
U.S. Appl. No. 16/305,002, filed Mar. 28, 2019.
U.S. Appl. No. 16/650,907, filed Mar. 26, 2020.
U.S. Appl. No. 16/762,694, filed May 8, 2020.
U.S. Appl. No. 16/767,527, filed May 27, 2020.
U.S. Appl. No. 17/293,996, filed May 14, 2021.

\* cited by examiner

CRYOPRESERVATION VESSEL

CROSS-REFERENCE TO RELATED APPLICATIONS

This patent application is the U.S. national phase of International Patent Application No. PCT/JP2017/021508, filed on Jun. 9, 2017, which claims the benefit of Japanese Patent Application No. 2016-118976, filed Jun. 15, 2016, the disclosures of which are incorporated herein by reference in their entireties for all purposes.

TECHNICAL FIELD

The present invention relates to vessels for cryopreserving cells or proteins.

BACKGROUND ART

In recent years, bio-pharmaceuticals and regenerative medicine have attracted increasing attention and have been actively researched and developed. In association with that, there has been an active development also in techniques for stably and long preserving cells or proteins obtained in the course of such researches and development.

Cryopreservation is a standard technique for stably preserving cells and proteins over a long period of time. For example, slow freezing and rapid freezing are known as methods for the cryopreservation of cells. In the slow freezing method, a cell suspension containing a low concentration of cryoprotectant such as dimethyl sulfoxide or glycerol is cooled and frozen slowly. The cryoprotectant suppresses rapid crystallization of intracellular and extracellular water, thus protecting the cells from damages. In the rapid freezing method, on the other hand, a cell suspension containing a high concentration of cryoprotectant is cooled and frozen rapidly. The method can prevent the cells from damages by solidifying and freezing water in the glass state without causing the water to crystallize. An example cryoprotectant used in the rapid freezing method is a high concentration of a combination of dimethyl sulfoxide, acetamide and propylene glycol. Furthermore, cryopreservation methods with improved vessels and procedures have been reported.

In the slow freezing method and the rapid freezing method, quick operation is required particularly during melting in order to avoid the osmotic toxicity of the cryoprotectant to the cells. To avoid this toxicity in cell freezing, a method has been reported in which cells are frozen and melted while avoiding a need of newly adding a fresh medium to the melted cells for the purpose of diluting the cryoprotectant. Specifically, a method has been reported which includes a step in which a cell solution containing a cryoprotectant is frozen, and a layer differing from the above solution in the type of medium or diluent is added to the frozen cell solution and is frozen thereon to form a double-layer frozen body (see, for example, Patent Literature 1).

A method for cryopreserving cells has been disclosed in which cells are cryopreserved using a microtiter plate pre-coated with poly-lysine. While poly-lysine is conventionally used as a coating which promotes the adhesion of cells to the surface of plastics and glass, it has been reported that poly-lysine improves, by a process that is independent of such cell adhesion, assay performance in melting even after prolonged cryopreservation, and that the use of a microtiter plate facilitates the cell cryopreservation operation (see, for example, Patent Literature 2).

Incidentally, cell culture vessels such as microtiter plates, and cryopreservation vessels such as test tubes are preferably treated to reduce the adhesiveness with respect to cells. For example, it has been reported that such treatment for reducing the adhesiveness for cells may be achieved by forming a coating layer using a water-soluble resin having an azide group as a photosensitive functional group because such a resin can form a uniform coating layer by irradiation with 300 to 500 nm light, and can reduce the amount of cell adhesion to allow cell aggregates to grow with enhanced efficiency (see, for example, Patent Literature 3).

CITATION LIST

Patent Literature

Patent Literature 1: Japanese Patent Kohyo Publication No. 2014-502610
Patent Literature 2: Japanese Patent Kohyo Publication No. 2012-512637
Patent Literature 3: WO 2015/178413

SUMMARY OF INVENTION

Technical Problem

The formation of coatings capable of inhibiting the adhesion of cells or proteins is also desirable for cryopreservation vessels. However, due to the fact that the coatings formed on cryopreservation vessels should be resistant not only to aqueous solvents but also to organic solvents (for example, cryoprotectants, in particular, dimethyl sulfoxide), there have been no cryopreservation vessels which have a coating satisfying all of these performances.

Solution to Problem

The present inventors have found that a cell or protein cryopreservation vessel having, on at least a portion of the surface thereof, a coating which includes a copolymer containing a specific anionic structure, a specific cationic structure and optionally a specific hydrophobic structure, exhibits excellent resistance to solvents (for example, cryoprotectants, in particular, dimethyl sulfoxide) and excellent resistance to the adhesion of cells or proteins. The present invention has been completed based on the finding.

Aspects of the present invention reside in the following.

[1] A cell or protein cryopreservation vessel comprising a coating on at least a portion of the surface thereof, wherein the coating comprises a copolymer including a repeating unit containing a group represented by the following formula (a), and a repeating unit containing a group represented by the following formula (b):

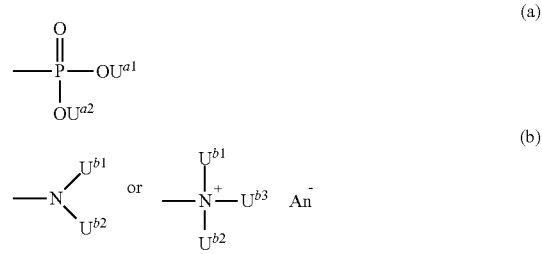

wherein $U^{a1}$, $U^{a2}$, $U^{b1}$, $U^{b2}$ and $U^{b3}$ are each independently a hydrogen atom or a $C_{1-5}$ linear or branched alkyl group, and An⁻ is an anion selected from the group consisting of halide ion, inorganic acid ion, hydroxide ion and isothiocyanate ion.

[2] The vessel described in [1], wherein the copolymer further includes a repeating unit containing a group represented by the following formula (c):

  (c)

wherein $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

[3] The vessel described in [1], wherein the copolymer includes repeating units represented by the following formulae (a1) and (b1):

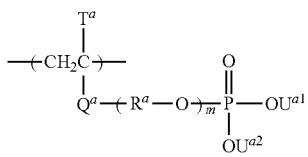 (a1)

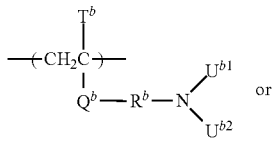 (b1)

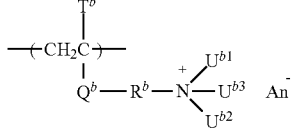

wherein $T^a$ and $T^b$ are each independently a hydrogen atom or a $C_{1-5}$ linear or branched alkyl group;

$Q^a$ and $Q^b$ are each independently a single bond, an ester bond or an amide bond;

$R^a$ and $R^b$ are each independently a $C_{1-10}$ linear or branched alkylene group which may be substituted with a halogen atom;

$U^{a1}$, $U^{a2}$, $U^{b1}$, $U^{b2}$ and $U^{b3}$ are each independently a hydrogen atom or a $C_{1-5}$ linear or branched alkyl group;

An⁻ is an anion selected from the group consisting of halide ion, inorganic acid ion, hydroxide ion and isothiocyanate ion; and m is an integer of 0 to 6.

[4] The vessel described in [2], wherein the copolymer further includes a repeating unit represented by the following formula (c1):

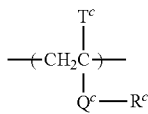 (c1)

wherein $T^c$ independently at each occurrence is a hydrogen atom or a $C_{1-5}$ linear or branched alkyl group;

$Q^c$ is a single bond, an ether bond or an ester bond; and $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

[5] The vessel described in [1], wherein the copolymer is one obtained by polymerizing a monomer mixture including compounds represented by the following formulae (A) and (B):

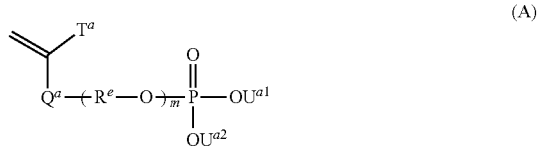 (A)

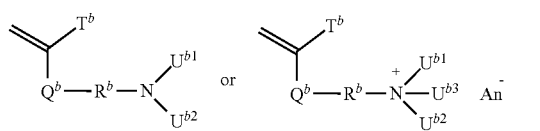 (B)

wherein $T^a$, $T^b$, $U^{a1}$, $U^{a2}$, $U^{b1}$, $U^{b2}$ and $U^{b3}$ are each independently a hydrogen atom or a $C_{1-5}$ linear or branched alkyl group;

$Q^a$ and $Q^b$ are each independently a single bond, an ester bond or an amide bond;

$R^a$ and $R^b$ are each independently a $C_{1-10}$ linear or branched alkylene group which may be substituted with a halogen atom;

An⁻ is an anion selected from the group consisting of halide ion, inorganic acid ion, hydroxide ion and isothiocyanate ion; and m is an integer of 0 to 6.

[6] The vessel described in [5], wherein the monomer mixture that is polymerized further includes a compound represented by the following formula (D) or (E):

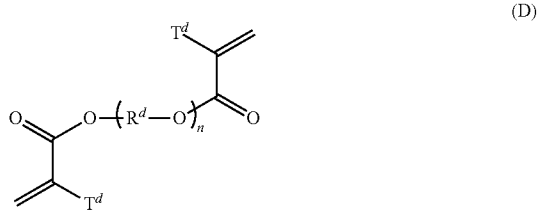 (D)

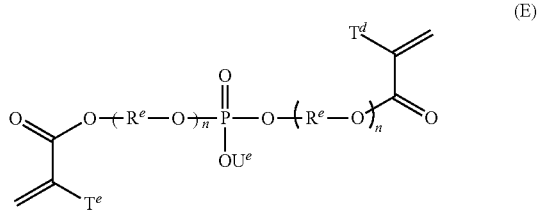 (E)

wherein $T^d$, $T^e$ and $U^e$ are each independently a hydrogen atom or a $C_{1-5}$ linear or branched alkyl group;

$R^d$ and $R^e$ are each independently a $C_{1-10}$ linear or branched alkylene group which may be substituted with a halogen atom; and n is an integer of 1 to 6.

[7] The vessel described in [5] or [6], wherein the monomer mixture that is polymerized further includes a compound represented by the following formula (C):

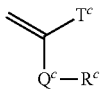
(C)

wherein $T^c$ independently at each occurrence is a hydrogen atom or a $C_{1-5}$ linear or branched alkyl group;

$Q^c$ is a single bond, an ether bond or an ester bond; and $R^c$ is a $C_{1-18}$ linear or branched alkyl group, a $C_{3-10}$ cyclic hydrocarbon group, a $C_{6-10}$ aryl group, a $C_{7-14}$ aralkyl group or a $C_{7-14}$ aryloxyalkyl group, wherein the aryl moiety may be substituted with a $C_{1-5}$ linear or branched alkyl group which may be substituted with a halogen atom.

[8] The vessel described in any one of [1] to [7], wherein the coating has a resistance to a cryoprotectant.

[9] The vessel described in [8], wherein the cryoprotectant is selected from the group consisting of ethylene glycol, propanediol, methanol, ethanol, dimethylacetamide, glycerol, polyethylene glycol, polyvinylpyrrolidone, hydroxyethyl starch, dextran, albumin, acetamide, acrylamide, propionamide, methacrylamide, isobutyramide, lactamide, nicotinamide, isophthalamide, acetonitrile, acetone and dimethyl sulfoxide.

A method for producing a cell or protein cryopreservation vessel, comprising:

a step of obtaining a copolymer by polymerizing a monomer mixture including compounds represented by the following formulae (A) and (B):

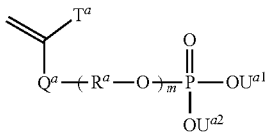
(A)

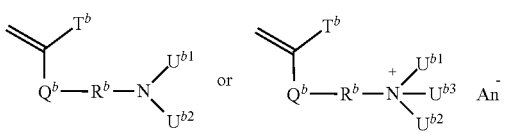
(B)

wherein $T^a$, $T^b$, $U^{a1}$, $U^{a2}$, $U^{b1}$, $U^{b2}$ and $U^{b3}$ are each independently a hydrogen atom or a $C_{1-5}$ linear or branched alkyl group;

$Q^a$ and $Q^b$ are each independently a single bond, an ester bond or an amide bond;

$R^a$ and $R^b$ are each independently a $C_{1-10}$ linear or branched alkylene group which may be substituted with a halogen atom;

$An^-$ is an anion selected from the group consisting of halide ion, inorganic acid ion, hydroxide ion and isothiocyanate ion; and m is an integer of 0 to 6; and a step of bringing the copolymer into contact with at least a portion of the surface of a cell or protein cryopreservation vessel to form a coating.

[11] The production method described in [10], wherein the monomer mixture further includes a compound represented by the following formula (D) or (E):

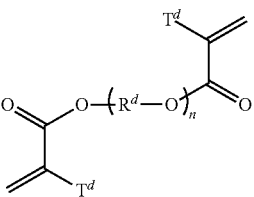
(D)

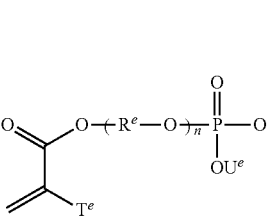
(E)

wherein $T^d$, $T^e$ and $U^e$ are each independently a hydrogen atom or a $C_{1-5}$ linear or branched alkyl group;

$R^d$ and $R^e$ are each independently a $C_{1-10}$ linear or branched alkylene group which may be substituted with a halogen atom; and n is an integer of 1 to 6.

The production method described in [10] or [11], wherein the monomer mixture further includes a compound represented by the following formula (C):

(C)

wherein $T^c$ independently at each occurrence is a hydrogen atom or a $C_{1-5}$ linear or branched alkyl group;

$Q^c$ is a single bond, an ether bond or an ester bond; and $R^c$ is a $C_{1-18}$ linear or branched alkyl group, a $C_{3-10}$ cyclic hydrocarbon group, a $C_{6-10}$ aryl group, a $C_{7-14}$ aralkyl group or a $C_{7-14}$ aryloxyalkyl group, wherein the aryl moiety may be substituted with a $C_{1-5}$ linear or branched alkyl group which may be substituted with a halogen atom.

Advantageous Effects of Invention

The cell or protein cryopreservation vessels of the present invention exhibit an outstanding resistance to the adhesion of cells or proteins by virtue of having, on at least a portion of the surface thereof, a coating which includes a copolymer containing a specific anionic structure, a specific cationic structure and optionally a specific hydrophobic structure. The cell or protein cryopreservation vessels of the present invention can contain a suspension or solution of cells or proteins without allowing the cells or proteins to adhere to the surface of the vessel (the surface which can be brought into contact with the suspension or solution of cells or proteins) during freezing, preservation and melting steps, thus making it possible to recover the cells or proteins from the suspension or solution efficiently. Further, the copolymer can be firmly fixed to resins such as plastics and metals such as stainless steel, and can easily form a coating on at least a portion of the surface of the vessel. Furthermore, the coating is highly resistant not only to aqueous solvents but also to organic solvents (for example, cryoprotectants, in particular, dimethyl sulfoxide), and is therefore stable and does not adversely affect the cells or proteins during the steps of freezing, preservation and melting of cells or proteins.

DESCRIPTION OF EMBODIMENTS

《Description of Terms》

Figure 1:
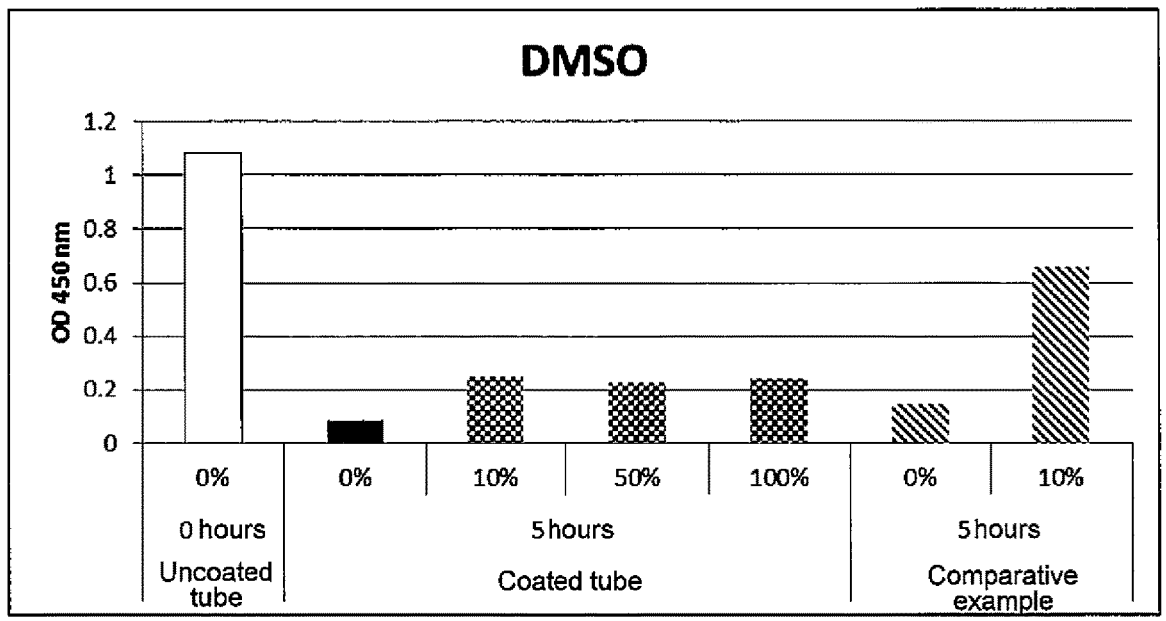
FIG. 1 is a graph which shows the results of measurement of the amounts of protein adhesion to coated tubes of Example 1, an uncoated tube and tubes of Comparative Example after treatment with dimethyl sulfoxide (DMSO, 0, 10, 50 and 100%) as described in Test Example 4.
Figure 2:
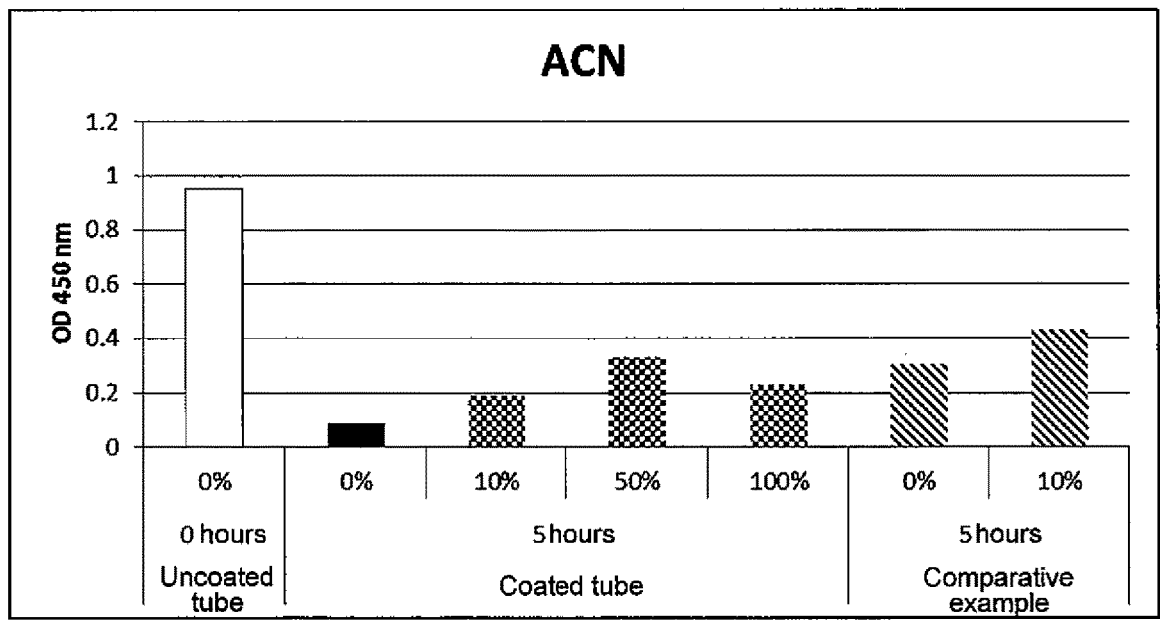
FIG. 2 is a graph which shows the results of measurement of the amounts of protein adhesion to coated tubes of Example 1, an uncoated tube and tubes of Comparative Example after treatment with acetonitrile (ACN, 0, 10, 50 and 100%) as described in Test Example 4.
Figure 3:
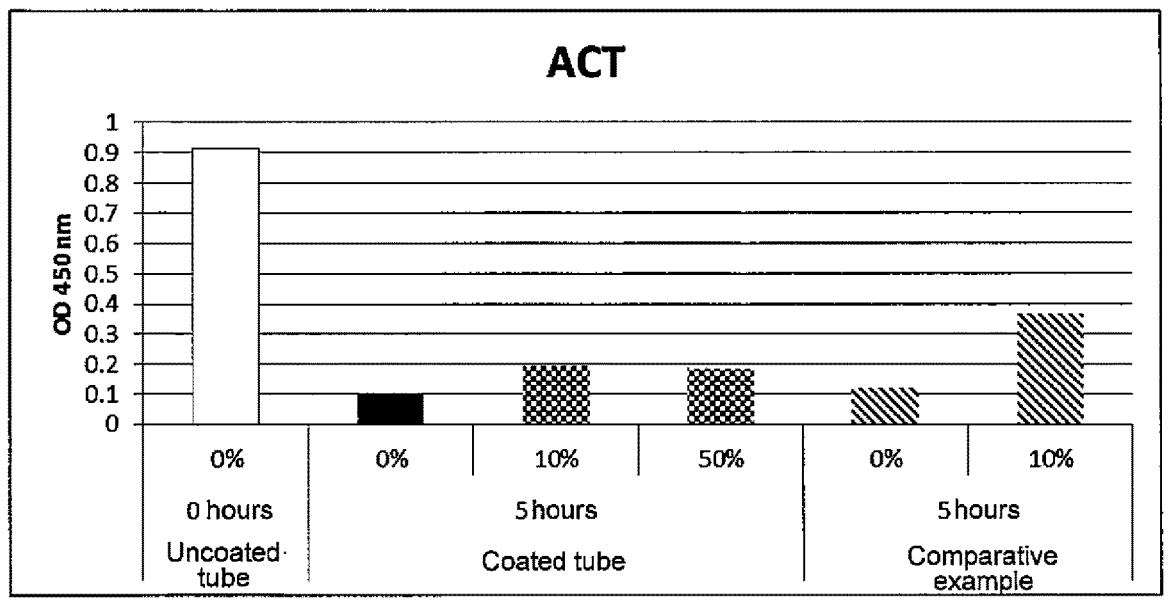
FIG. 3 is a graph which shows the results of measurement of the amounts of protein adhesion to coated tubes of Example 1, an uncoated tube and tubes of Comparative Example after treatment with acetone (ACT, 0, 10 and 50%) as described in Test Example 4.
Figure 4:
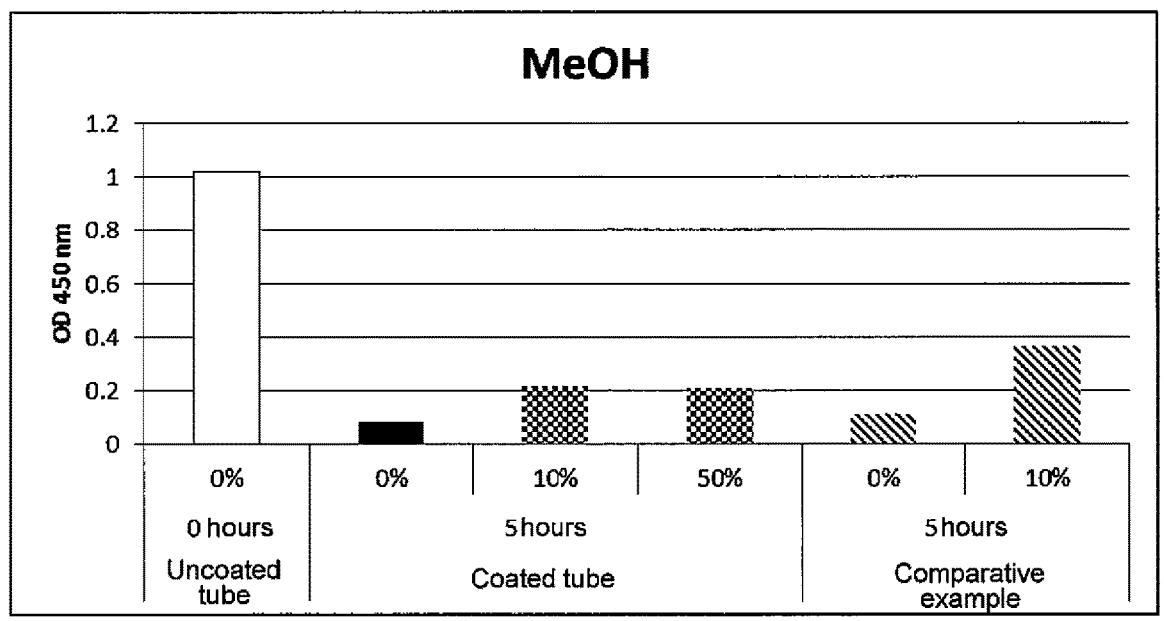
FIG. 4 is a graph which shows the results of measurement of the amounts of protein adhesion to coated tubes of Example 1, an uncoated tube and tubes of Comparative Example after treatment with methanol (MeOH, 0, 10 and 50%) as described in Test Example 4.
Figure 5:
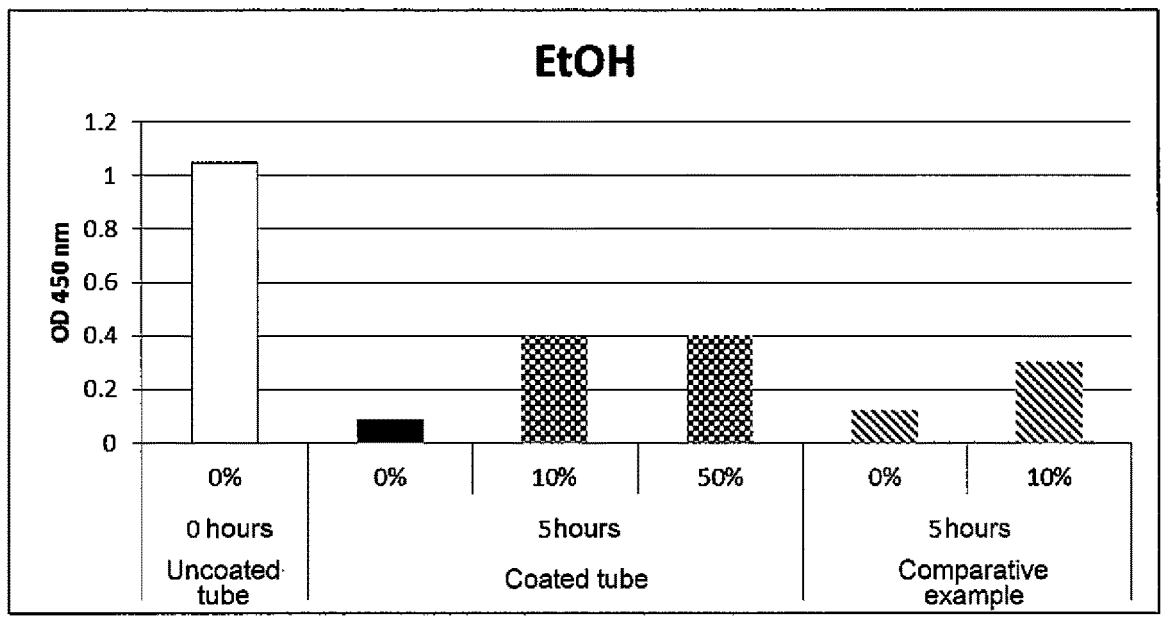
FIG. 5 is a graph which shows the results of measurement of the amounts of protein adhesion to coated tubes of Example 1, an uncoated tube and tubes of Comparative Example after treatment with ethanol (EtOH, 0, 10 and 50%) as described in Test Example 4.

The terms used in the present invention have the following definitions unless otherwise specified.

In the present invention, the "halogen atom" means fluorine atom, chlorine atom, bromine atom or iodine atom.

In the present invention, the "alkyl group" means linear or branched, monovalent saturated aliphatic hydrocarbon group. Examples of the "$C_{1-5}$ linear or branched alkyl groups" include methyl group, ethyl group, n-propyl group, isopropyl group, n-butyl group, isobutyl group, s-butyl group, t-butyl group, n-pentyl group, 1-methylbutyl group, 2-methylbutyl group, 3-methylbutyl group, 1,1-dimethylpropyl group, 1,2-dimethylpropyl group, 2,2-dimethylpropyl group and 1-ethylpropyl group. Examples of the "$C_{1-18}$ linear or branched alkyl groups" include the $C_{1-5}$ linear or branched alkyl groups mentioned above, and further include hexyl group, heptyl group, octyl group, nonyl group, decyl group, undecyl group, dodecyl group, tridecyl group, tetradecyl group, pentadecyl group, hexadecyl group, heptadecyl group, octadecyl group, and isomers thereof. Similarly, examples of the "$C_{1-10}$ linear or branched alkyl groups" include the "$C_{1-5}$ linear or branched alkyl groups" mentioned above, and further include hexyl group, heptyl group, octyl group, nonyl group, decyl group, and isomers thereof.

In the present invention, the "$C_{1-5}$ linear or branched alkyl group which may be substituted with a halogen atom" means any of the above-mentioned $C_{1-5}$ linear or branched alkyl groups, or any of the above-mentioned $C_{1-5}$ linear or branched alkyl groups that are substituted with one or more of the above-mentioned halogen atoms. Examples of the "$C_{1-5}$ linear or branched alkyl groups" are as mentioned above. The "$C_{1-5}$ linear or branched alkyl group substituted with one or more halogen atoms" means any of the above-mentioned $C_{1-5}$ linear or branched alkyl groups that are substituted with a halogen atom in place of one or more hydrogen atoms, with examples including fluoromethyl group, difluoromethyl group, trifluoromethyl group, chloromethyl group, dichloromethyl group, trichloromethyl group, bromomethyl group, iodomethyl group, 2,2,2-trifluoroethyl group, 2,2,2-trichloroethyl group, perfluoroethyl group, perfluorobutyl group and perfluoropentyl group.

In the present invention, the "ester bond" means —C(=O)—O— or —O—C(=O)—, the "amide bond" means —NHC(=O)— or —C(=O)NH—, and the ether bond means —O—.

In the present invention, the "$C_{1-10}$ linear or branched alkylene group which may be substituted with a halogen atom" means a $C_{1-10}$ linear or branched alkylene group, or a $C_{1-10}$ linear or branched alkylene group substituted with one or more halogen atoms. Here, the "alkylene group" means a divalent organic group corresponding to the alkyl group described hereinabove. Examples of the "$C_{1-10}$ linear or branched alkylene groups" include methylene group, ethylene group, propylene group, trimethylene group, tetramethylene group, 1-methylpropylene group, 2-methylpropylene group, dimethylethylene group, ethylethylene group, pentamethylene group, 1-methyl-tetramethylene group, 2-methyl-tetramethylene group, 1,1-dimethyl-trimethylene group, 1,2-dimethyl-trimethylene group, 2,2-dimethyl-trimethylene group, 1-ethyl-trimethylene group, hexamethylene group, octamethylene group and decamethylene group. Of these, ethylene group, propylene group, octamethylene group and decamethylene group are preferable. $C_{1-5}$ linear or branched alkylene groups such as, for example, ethylene group, propylene group, trimethylene group and tetramethylene group are more preferable. Ethylene group and propylene group are particularly preferable. The "$C_{1-10}$ linear or branched alkylene group substituted with one or more halogen atoms" means any of the above-mentioned alkylene groups that are substituted with a halogen atom in place of one or more hydrogen atoms, and, in particular, ethylene or propylene group substituted with a halogen atom in place of part or all of the hydrogen atoms are preferable.

In the present invention, the "$C_{3-10}$ cyclic hydrocarbon group" means a $C_{3-10}$ monocyclic or polycyclic, saturated or partially unsaturated, monovalent aliphatic hydrocarbon group. Of such groups, $C_{3-10}$ monocyclic or bicyclic, saturated monovalent aliphatic hydrocarbon groups are preferable, with examples including $C_{3-10}$ cycloalkyl groups such as cyclopropyl group, cyclobutyl group and cyclohexyl group, and $C_{4-10}$ bicycloalkyl groups such as bicyclo[3.2.1]octyl group, bornyl group and isobornyl group.

In the present invention, the "$C_{6-10}$ aryl group" means a $C_{6-10}$ monocyclic or polycyclic, monovalent aromatic hydrocarbon group, with examples including phenyl group, naphthyl group and anthryl group. The "$C_{6-10}$ aryl group" may be substituted with one or more of the above-mentioned "$C_{1-5}$ linear or branched alkyl groups which may be substituted with a halogen atom".

In the present invention, the "$C_{7-15}$ aralkyl group" means group —R—R' wherein R represents the "$C_{1-5}$ alkylene group" described hereinabove, and R' represents the "$C_{6-10}$ aryl group" described hereinabove, with examples including benzyl group, phenethyl group and α-methylbenzyl group. The aryl moiety of the "$C_{7-15}$ aralkyl group" may be substituted with one or more of the "$C_{1-5}$ linear or branched alkyl groups which may be substituted with a halogen atom" described hereinabove.

In the present invention, the "$C_{7-15}$ aryloxyalkyl group" means group —R—O—R' wherein R represents the "$C_{1-5}$ alkylene group" described hereinabove, and R' represents the "$C_{6-10}$ aryl group" described hereinabove, with examples including phenoxymethyl group, phenoxyethyl group and phenoxypropyl group. The aryl moiety of the "$C_{7-15}$ aryloxyalkyl group" may be substituted with one or more of the "$C_{1-5}$ linear or branched alkyl groups which may be substituted with a halogen atom" described hereinabove.

In the present invention, the "halide ion" means fluoride ion, chloride ion, bromide ion or iodide ion.

In the present invention, the "inorganic acid ion" means carbonate ion, sulfate ion, phosphate ion, hydrogen phosphate ion, dihydrogen phosphate ion, nitrate ion, perchlorate ion or borate ion.

The anion $An^-$ is preferably a halide ion, a sulfate ion, a phosphate ion, a hydroxide ion or an isothiocyanate ion, and particularly preferably a halide ion.

In the present invention, the (meth)acrylate compounds mean both acrylate compounds and methacrylate compounds. For example, (meth)acrylic acid means acrylic acid and methacrylic acid.

Examples of the proteins in the present invention include fibrinogen, bovine serum albumin (BSA), human albumin, various globulins, β-lipoprotein, various antibodies (IgG, IgA, IgM), peroxidase, various complements, various lectins, fibronectin, lysozyme, von Willebrand factor (vWF), serum γ-globulin, pepsin, ovalbumin, insulin, histone, ribonuclease, collagen and cytochrome c.

Examples of the cells include fibroblasts, bone marrow cells, B lymphocytes, T lymphocytes, neutrophils, red blood cells, platelets, macrophages, monocytes, bone cells, bone marrow cells, pericytes, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocyte, microglia, astroglial cells, heart cells, esophagus cells, muscle cells (for example, smooth muscle cells and skeletal muscle cells), pancreatic beta cells, melanocytes, hematopoietic precursor cells, mononuclear cells, embryonic stem cells (ES cells), embryonic tumor cells, embryonic germline stem cells, induced pluripotent stem cells (iPS cells), neural stem cells, hematopoietic stem cells, mesenchymal stem cells, liver stem cells, pancreatic stem cells, muscle stem cells, germline stem cells, intestinal stem cells, cancer stem cells, hair follicle stem cells, megakaryocytes, CD34 positive spinal cord-derived megakaryocytes, and various cell lines (for example, HCT116, Huh7, HEK293 (human embryonic kidney cells), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, S2, Sf9, Sf21, High Five, Vero).

《Description of Invention》

The cryopreservation vessel of the present invention is not particularly limited as long as at least a portion of the surface thereof has a coating which includes a polymer capable of inhibiting the adhesion of the cells or proteins described above.

In the present specification, examples of the polymers capable of inhibiting the adhesion of cells or proteins include polymers of ethylenically unsaturated monomers, and polysaccharides and derivatives thereof. Examples of the polymers of ethylenically unsaturated monomers include polymers of one, or two or more kinds of ethylenically unsaturated monomers selected from the group consisting of (meth)acrylic acid and esters thereof; vinyl acetate; vinylpyrrolidone; ethylene; vinyl alcohols; and hydrophilic functional derivatives thereof. Examples of the polysaccharides and derivatives thereof include cellulose polymers such as hydroxyalkylcelluloses (for example, hydroxyethylcellulose and hydroxypropylcellulose), starch, dextran and curdlan.

Examples of the hydrophilic functional groups in the hydrophilic functional derivatives include phosphoric acid, phosphonic acid, and ester structures of these acids; betaine structures; amide structures; alkylene glycol residues; amino groups; and sulfinyl groups.

Here, the phosphoric acid and ester structures thereof mean groups represented by the following formula:

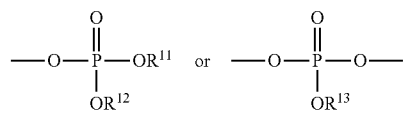

wherein $R^{11}$, $R^{12}$ and $R^{13}$ are each independently a hydrogen atom or an organic group (such as, for example, a $C_{1-5}$ linear or branched alkyl group). The phosphonic acid and ester structures thereof mean groups represented by the following formula:

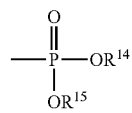

wherein $R^{14}$ and $R^{15}$ are each independently a hydrogen atom or an organic group (such as, for example, a $C_{1-5}$ linear or branched alkyl group). Examples of the ethylenically unsaturated monomers having such a structure include acid phosphoxyethyl (meth)acrylate and vinylphosphonic acid.

The betaine structures mean monovalent or divalent groups of compounds having an amphoteric center between a quaternary ammonium cation structure and an acid anionic structure, with examples including phosphorylcholine group:

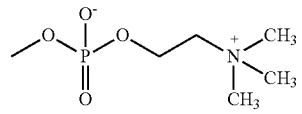

Examples of the ethylenically unsaturated monomers having such a structure include 2-methacryloyloxyethyl phosphorylcholine (MPC).

The amide structures mean groups represented by the following formula:

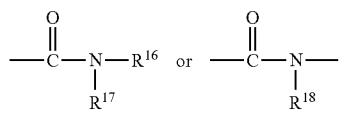

wherein $R^{16}$, $R^{17}$ and $R^{18}$ are each independently a hydrogen atom or an organic group (such as, for example, a methyl group, a hydroxymethyl group or a hydroxyethyl group). Examples of the ethylenically unsaturated monomers having such a structure include (meth)acrylamide and N-(hydroxymethyl) (meth)acrylamide. Further, monomers or polymers having such a structure are disclosed in, for example, Japanese Patent Application Kokai Publication No. 2010-169604.

The alkylene glycol residues mean alkyleneoxy groups (—Alk—O—) which remain after the hydroxyl group(s) at one or both ends of an alkylene glycol (HO—Alk—OH; wherein Alk is a $C_{1-10}$ alkylene group) has condensed with other compound. The residues also include poly(alkyleneoxy) groups having alkyleneoxy repeating units. Examples of the ethylenically unsaturated monomers having such a structure include 2-hydroxyethyl (meth)acrylate and methoxypolyethylene glycol (meth)acrylate. Further, monomers or polymers having such a structure are disclosed in, for example, Japanese Patent Application Kokai Publication No. 2008-533489.

The amino groups mean groups represented by the formula: —$NH_2$, —$NHR^{19}$ or —$NR^{20}R^{21}$ wherein $R^{19}$, $R^{20}$ and $R^{21}$ are each independently an organic group (such as, for example, a $C_{1-5}$ linear or branched alkyl group). The amino groups in the present specification include quaternarized or chlorinated amino groups. Examples of the ethylenically unsaturated monomers having such a structure include dimethylaminoethyl (meth)acrylate, 2-(t-butylamino)ethyl (meth)acrylate and methacrylylcholine chloride.

The sulfinyl groups mean groups represented by the following formula:

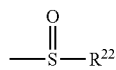

wherein $R^{22}$ is an organic group (such as, for example, a $C_{1-10}$ organic group, preferably a $C_{1-10}$ alkyl group having one or more hydroxyl groups). Examples of the polymers having such a structure include copolymers disclosed in Japanese Patent Application Kokai Publication No. 2014-48278.

In particular, the copolymer preferably includes a repeating unit containing a group represented by the following formula (a), and a repeating unit containing a group represented by the following formula (b):

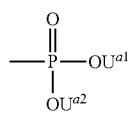

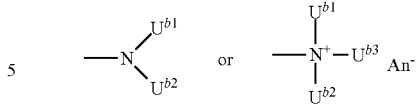

In the formulae, $U^{a1}$, $U^{a2}$, $U^{b1}$, $U^{b2}$ and $U^{b3}$ are each independently a hydrogen atom or a $C_{1-5}$ linear or branched alkyl group; and $An^-$ is an anion selected from the group consisting of halide ion, inorganic acid ion, hydroxide ion and isothiocyanate ion.

The copolymer may further include a repeating unit containing a group represented by the following formula (c):

wherein $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

The copolymer associated with the cryopreservation vessel of the present invention is not particularly limited as long as the copolymer includes a repeating unit containing a group represented by the above formula (a), a repeating unit containing a group represented by the above formula (b), and optionally a repeating unit containing a group represented by the above formula (c). In the present invention, the repeating unit containing a group represented by the above formula (c) is different from the repeating unit containing a group represented by the above formula (a), and from the repeating unit containing a group represented by the above formula (b). The copolymer is preferably one obtained by the radical polymerization of a monomer containing a group represented by the above formula (a), a monomer containing a group represented by the above formula (b), and optionally a monomer containing a group represented by the above formula (c). Polymers obtained by polycondensation or polyaddition reaction may be also used. Examples of the copolymers include vinyl polymerized polymers obtained by the reaction of olefins, and also include polyamides, polyesters, polycarbonates and polyurethanes. Of these, vinyl polymerized polymers obtained by the reaction of olefins, or (meth)acrylate polymers obtained by the polymerization of (meth)acrylate compounds are preferable.

In the copolymer, the proportion of the repeating units containing a group represented by the formula (a) is 3 mol % to 80 mol %. The copolymer may include two or more kinds of repeating units containing a group represented by the formula (a).

In the copolymer, the proportion of the repeating units containing a group represented by the formula (b) is 3 mol % to 80 mol %. The copolymer may include two or more kinds of repeating units containing a group represented by the formula (b).

In the copolymer, the proportion of the repeating units containing a group represented by the formula (c) may be the balance after deduction of the units having the formulae (a) and (b) from the copolymer, and is, for example, 0 mol % to 90 mol %. The copolymer may include two or more kinds of repeating units containing a group represented by the formula (c).

In a preferred embodiment of the copolymer associated with the cryopreservation vessel of the invention, the copolymer includes repeating units represented by the following formulae (a1) and (b1):

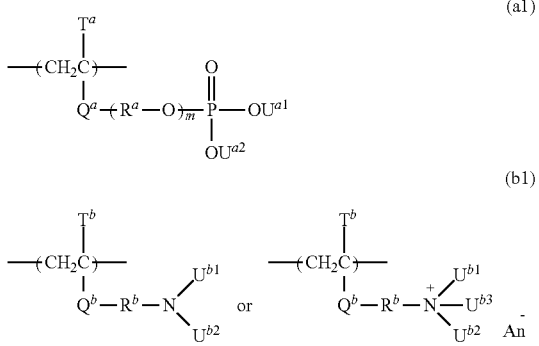

(a1)

(b1)

In the formulae, $T^a$ and $T^b$ are each independently a hydrogen atom or a $C_{1-5}$ linear or branched alkyl group, $Q^a$ and $Q^b$ are each independently a single bond, an ester bond or an amide bond, $R^a$ and $R^b$ are each independently a $C_{1-10}$ linear or branched alkylene group which may be substituted with a halogen atom, $U^{a1}$, $U^{a2}$, $U^{b1}$, $U^{b2}$ and $U^{b3}$ are each independently a hydrogen atom or a $C_{1-5}$ linear or branched alkyl group, $An^-$ is an anion selected from the group consisting of halide ion, inorganic acid ion, hydroxide ion and isothiocyanate ion, and m is an integer of 0 to 6.

The copolymer may further include repeating units of the formula (c1) below:

(c1)

In the formula, $T^c$ independently at each occurrence is a hydrogen atom or a $C_{1-5}$ linear or branched alkyl group, $Q^c$ is a single bond, an ether bond or an ester bond, and $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

In the formula (a1), m is an integer of 0 to 6, preferably an integer of 1 to 6, more preferably an integer of 1 to 5, and particularly preferably 1.

In the copolymer, the proportion of the repeating units represented by the formula (a1) is 3 mol % to 80 mol %. The copolymer may include two or more kinds of repeating units represented by the formula (a1).

In the copolymer, the proportion of the repeating units represented by the formula (b1) is 3 mol % to 80 mol %. The copolymer may include two or more kinds of repeating units represented by the formula (b1).

In the copolymer, the proportion of the repeating units represented by the formula (c1) may be the balance after deduction of the units having the formulae (a1) and (b1) from the copolymer, and is, for example, 0 mol % to 90 mol %. The copolymer may include two or more kinds of repeating units represented by the formula (c1).

In another preferred embodiment of the copolymer associated with the cryopreservation vessel of the invention, the copolymer is one obtained by reacting (polymerizing) in a solvent a monomer mixture including compounds represented by the following formulae (A) and (B):

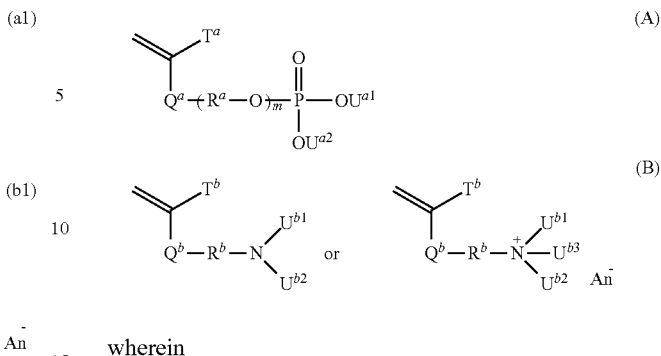

(A)

(B)

wherein $T^a$ and $T^b$ are each independently a hydrogen atom or a $C_{1-5}$ linear or branched alkyl group;

$Q^a$ and $Q^b$ are each independently a single bond, an ester bond or an amide bond;

$R^a$ and $R^b$ are each independently a $C_{1-10}$ linear or branched alkylene group which may be substituted with a halogen atom;

$U^{a1}$, $U^{a2}$, $U^{b1}$, $U^{b2}$ and $U^{b3}$ are each independently a hydrogen atom or a $C_{1-5}$ linear or branched alkyl group;

$An^-$ is an anion selected from the group consisting of halide ion, inorganic acid ion, hydroxide ion and isothiocyanate ion; and m is an integer of 0 to 6.

The monomer mixture that is polymerized may further include a compound represented by the following formula (C):

[Chem. 21]

(C)

wherein $T^c$ independently at each occurrence is a hydrogen atom or a $C_{1-5}$ linear or branched alkyl group;

$Q^c$ is a single bond, an ether bond or an ester bond; and $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

$T^a$, $T^b$ and $T^c$ are preferably each a hydrogen atom, a methyl group or an ethyl group, and more preferably a hydrogen atom or a methyl group. $Q^a$, $Q^b$ and $Q^c$ are preferably each a single bond or an ester bond, and more preferably an ester bond. $R^a$ and $R^b$ are preferably each a $C_{1-5}$ linear or branched alkylene group, and more preferably a methylene group, an ethylene group or a propylene group. $R^c$ is preferably a $C_{4-18}$ linear or branched alkyl group or a $C_{3-10}$ cycloalkyl group, and more preferably a butyl, pentyl or hexyl group or an isomer thereof, or a cyclohexyl group. $U^{a1}$, $U^{a2}$, $U^{b1}$, $U^{b2}$ and $U^{b3}$ are preferably each a hydrogen atom, a methyl group, an ethyl group or a t-butyl group. $U^{a1}$ and $U^{a2}$ in the formula (a) are more preferably each a hydrogen atom, and $U^{b1}$, $U^{b2}$ and $U^{b3}$ in the formula (b) are more preferably each a hydrogen atom, a methyl group, an ethyl group or a t-butyl group.

Specific examples of the formula (A) described above include vinylphosphonic acid, acid phosphoxyethyl (meth)

acrylate, 3-chloro-2-acid phosphoxypropyl (meth)acrylate, acid phosphoxypropyl (meth)acrylate, acid phosphoxymethyl (meth)acrylate, acid phosphoxypolyoxyethylene glycol mono(meth)acrylate and acid phosphoxypolyoxypropylene glycol mono(meth)acrylate. Of these, vinylphosphonic acid, acid phosphoxyethyl methacrylate (=2-(methacryloyloxy)ethyl phosphate) and acid phosphoxypolyoxyethylene glycol monomethacrylate are preferably used, and acid phosphoxyethyl methacrylate (=2-(methacryloyloxy)ethyl phosphate) is most preferable.

The structures of vinylphosphonic acid, acid phosphoxyethyl methacrylate (=2-(methacryloyloxy)ethyl phosphate), acid phosphoxypolyoxyethylene glycol monomethacrylate and acid phosphoxypolyoxypropylene glycol monomethacrylate are represented by the following formulae (A-1) to (A-4), respectively.

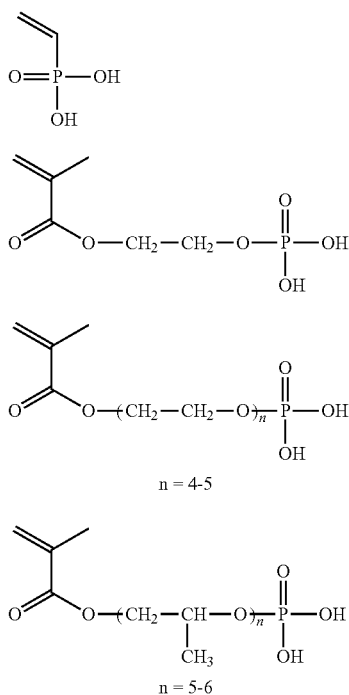

These compounds sometimes contain (meth)acrylate compounds with two functional groups of the general formula (D) or (E) described later which are formed during the synthesis.

Specific examples of the formula (B) described above include dimethylaminoethyl (meth)acrylate, diethylaminoethyl (meth)acrylate, dimethylaminopropyl (meth)acrylate, 2-(t-butylamino)ethyl (meth)acrylate and methacryloylcholine chloride. Of these, dimethylaminoethyl (meth)acrylate, methacryloylcholine chloride and 2-(t-butylamino)ethyl (meth)acrylate are preferably used, and dimethylaminoethyl (meth)acrylate is most preferably used.

The structures of dimethylaminoethyl acrylate (=acrylic acid 2-(dimethylamino)ethyl), diethylaminoethyl methacrylate (=methacrylic acid 2-(diethylamino)ethyl), dimethylaminoethyl methacrylate (=methacrylic acid 2-(dimethylamino)ethyl), methacryloylcholine chloride and 2-(t-butylamino)ethyl methacrylate (=methacrylic acid 2-(t-butylamino)ethyl) are represented by the following formulae (B-1) to (B-5), respectively.

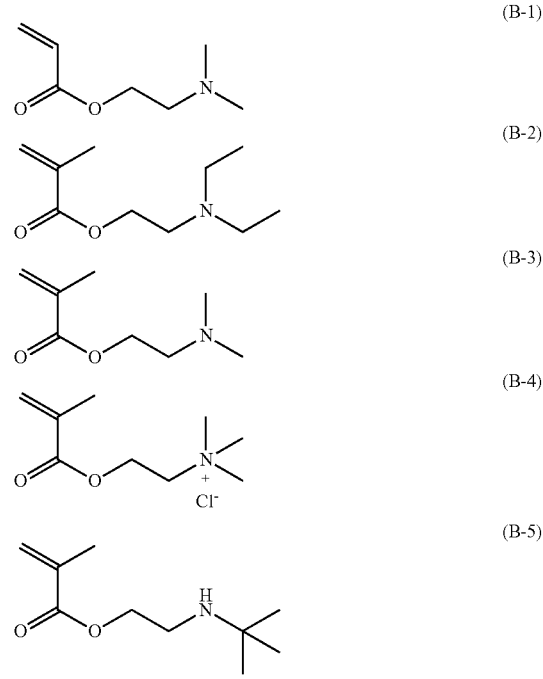

Specific examples of the formula (C) described above include linear or branched alkyl esters of (meth)acrylic acid such as butyl (meth)acrylate, 2-ethylhexyl (meth)acrylate, lauryl (meth)acrylate and stearyl (meth)acrylate; cyclic alkyl esters of (meth)acrylic acid such as cyclohexyl (meth)acrylate and isobornyl (meth)acrylate; aralkyl esters of (meth)acrylic acid such as benzyl (meth)acrylate and phenethyl (meth)acrylate; styrene monomers such as styrene, methylstyrene and chloromethylstyrene; vinyl ether monomers such as methyl vinyl ether and butyl vinyl ether; and vinyl ester monomers such as vinyl acetate and vinyl propionate. Of these, butyl (meth)acrylate and cyclohexyl (meth)acrylate are preferably used.

The structures of butyl methacrylate (=methacrylic acid butyl) and cyclohexyl methacrylate (=methacrylic acid cyclohexyl) are represented by the following formulae (C-1) and (C-2), respectively.

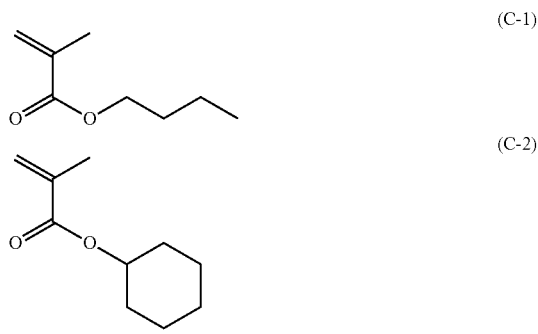

In another embodiment of the copolymer in the present invention, the copolymer may further include a desired fourth component in addition to the compounds represented by the formulae (A) and (B) and the optional compound of the formula (C). For example, the copolymer may be such that a (meth)acrylate compound having two or more functional groups is copolymerized as a fourth component, and part of the polymer is partially three-dimensionally cross-linked. Examples of such fourth components include bifunctional monomers represented by the following formula (D) or (E):

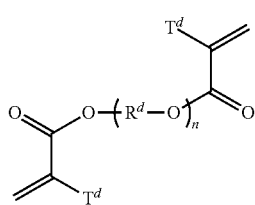
(D)

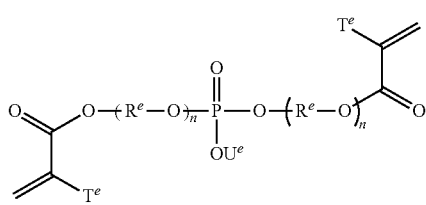
(E)

wherein $T^d$, $T^e$ and $U^e$ are each independently a hydrogen atom or a $C_{1-5}$ linear or branched alkyl group, $R^d$ and $R^e$ are each independently a $C_{1-10}$ linear or branched alkylene group which may be substituted with a halogen atom; and n is an integer of 1 to 6. That is, the copolymer according to the present invention preferably includes a crosslinked structure derived from such a bifunctional monomer.

In the formulae (D) and (E), $T^d$ and $T^e$ are preferably each independently a hydrogen atom, a methyl group or an ethyl group, and more preferably each independently a hydrogen atom or a methyl group.

In the formula (E), $U^e$ is preferably a hydrogen atom, a methyl group or an ethyl group, and more preferably a hydrogen atom.

In the formula (D), $R^d$ is preferably a $C_{1-3}$ linear or branched alkylene group which may be substituted with a halogen atom, and is more preferably independently at each occurrence an ethylene or propylene group or an ethylene or propylene group substituted with one chlorine atom, and is particularly preferably an ethylene group or a propylene group. In the formula (D), n is preferably an integer of 1 to 5, and particularly preferably 1.

In the formula (E), $R^e$ is preferably a $C_{1-3}$ linear or branched alkylene group which may be substituted with a halogen atom, and is more preferably independently at each occurrence an ethylene or propylene group or an ethylene or propylene group substituted with one chlorine atom, and is particularly preferably an ethylene group or a propylene group. In the formula (E), n is preferably an integer of 1 to 5, and particularly preferably 1.

Some preferred bifunctional monomers represented by the formula (D) are ethylene glycol di(meth)acrylate, triethylene glycol di(meth)acrylate and propylene glycol di(meth)acrylate.

Some preferred bifunctional monomers represented by the formula (E) are bis(methacryloyloxymethyl) phosphate, bis[(2-methacryloyloxy)ethyl] phosphate, bis[3-(methacryloyloxy)propyl] phosphate, and bifunctional monomers derived from the above formula (A-3) or (A-4).

Of the monomers represented by the formulae (D) and (E), the bifunctional monomers represented by the formula (E) are more preferably used.

An example trifunctional (meth)acrylate compound is phosphinylidine tris(oxy-2,1-ethanediyl) triacrylate.

Particularly preferred fourth components are ethylene glycol dimethacrylate, dimethacrylates which are bifunctional monomers derived from the formula (A-3) or (A-4) and have ethylene glycol or propylene glycol repeating units, bis[2-(methacryloyloxy)ethyl] phosphate, and dimethacrylates which are bifunctional monomers derived from the formula (A-3) or (A-4) and have ethylene glycol or propylene glycol repeating units via a phosphate group. The structures of these monomers are represented by the following formulae (D-1) to (D-3) and (E-1) to (E-3), respectively.

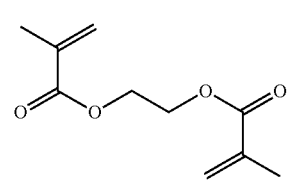
(D-1)

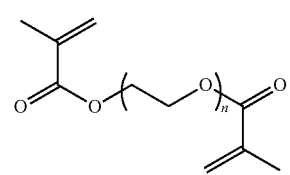
(D-2)

n = 4-5

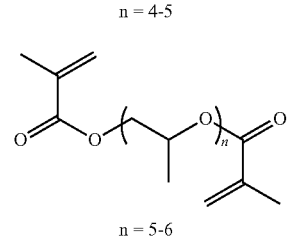
(D-3)

n = 5-6

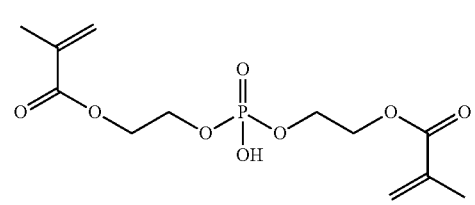
(E-1)

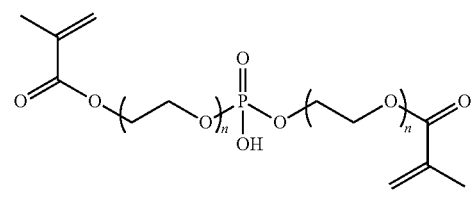
(E-2)

n = 4-5

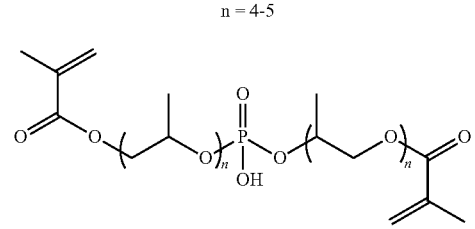
(E-3)

n = 5-6

Of the above monomers, those of the formulae (E-1) to (E-3) are particularly preferable.

The copolymer may include one, or two or more kinds of fourth components.

In the copolymer, the proportion of the crosslinked structure derived from the fourth component, for example, a bifunctional monomer represented by the formula (D) or (E), is 0 mol % to 50 mol %, preferably 5 mol % to 45 mol %, and most preferably 10 mol % to 40 mol %.

The proportion of the compound of the formula (A) relative to all the monomers forming the copolymer is 3 mol % to 80 mol %. The copolymer may include two or more kinds of compounds represented by the formula (A).

The proportion of the compound of the formula (B) relative to all the monomers forming the copolymer is 3 mol % to 80 mol %. The copolymer may include two or more kinds of compounds represented by the formula (B).

The proportion of the compound of the formula (C) relative to all the monomers forming the copolymer may be the balance after deduction of the proportions of the compounds of the formulae (A) and (B), and is, for example, 0 mol % to 90 mol %. The copolymer may include two or more kinds of compounds represented by the formula (C).

The copolymer according to the embodiments of the present invention may be synthesized by a method generally adopted for the synthesis of polymers such as acrylic polymers or methacrylic polymers, with examples including radical polymerization, anionic polymerization and cationic polymerization. The polymerization may be performed in various forms such as solution polymerization, suspension polymerization, emulsion polymerization and bulk polymerization.

The solvent used in the polymerization reaction may be water, phosphate buffered solution, alcohol such as ethanol, or a mixture of these solvents, and desirably includes water or ethanol. It is preferable that the solvent include 10 mass % to 100 mass % water or ethanol. It is more preferable that the solvent include 50 mass % to 100 mass % water or ethanol. It is still more preferable that the solvent include 80 mass % to 100 mass % water or ethanol. It is furthermore preferable that the solvent include 90 mass % to 100 mass % water or ethanol. Preferably, the total of water and ethanol is 100 mass % of the solvent.

Regarding the reaction concentration, for example, the concentration of the compounds represented by the formula (A) or (B) in the reaction solvent is preferably controlled to 0.01 mass % to 4 mass %. If the concentration is above 4 mass %, for example, the copolymer may be gelled in the reaction solvent due to the strong associative properties of the phosphate groups in the compound of the formula (A). If the concentration is below 0.01 mass %, the varnish that is obtained has such a low concentration that it is difficult to prepare a coating film-forming composition which can form a coating film with a sufficient film thickness. The concentration is more preferably 0.01 mass % to 3 mass %, for example, 3 mass %, 2 mass % or 1 mass %.

The synthesis of the copolymer associated with the present invention may start with, for example, forming a salt described in the formula (1) below and polymerizing it optionally together with a compound represented by the formula (C) to give a copolymer.

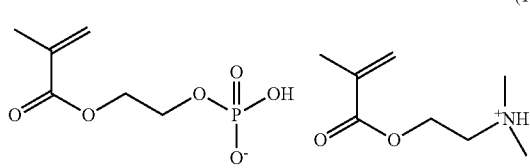

(1)

Because the phosphate group-containing monomer is associated easily, it may be added dropwise in small portions to the reaction solvent so that the monomer can be rapidly dispersed after its dropping to the reaction system.

The reaction solvent may be heated (for example, 40° C. to 100° C.) to increase the solubility of the monomers and the polymer.

To allow the polymerization reaction to proceed efficiently, it is preferable to use a polymerization initiator. Examples of the polymerization initiators include 2,2'-azobis(isobutyronitrile), 2,2'-azobis(2-methylbutyronitrile), 2,2'-azobis(2,4-dimethylvaleronitrile) (VA-065 manufactured by Wako Pure Chemical Industries, Ltd., 10 hour half-life temperature: 51° C.), 4,4'-azobis(4-cyanovaleric acid), 2,2'-azobis(4-methoxy-2,4-dimethylvaleronitrile), 1,1'-azobis(cyclohexane-1-carbonitrile), 1-[(1-cyano-1-methylethyl)azo]formamide, 2,2'-azobis[2-(2-imidazolin-2-yl)propane], 2,2'-azobis(2-methylpropionamidine) dihydrochloride, 2,2'-azobis[2-methyl-N-(2-hydroxyethyl)propionamide] (VA-086 manufactured by Wako Pure Chemical Industries, Ltd., 10 hour half-life temperature: 86° C.), benzoyl peroxide (BPO), 2,2'-azobis[N-(2-carboxyethyl)-2-methylpropionamidine] n-hydrate (VA-057 manufactured by Wako Pure Chemical Industries, Ltd., 10 hour half-life temperature: 57° C.), 4,4'-azobis(4-cyanopentanoic acid) (V-501 manufactured by Wako Pure Chemical Industries, Ltd.), 2,2'-azobis[2-(2-imidazolin-2-yl)propane] dihydrochloride (VA-044 manufactured by Wako Pure Chemical Industries, Ltd., 10 hour half-life temperature: 44° C.), 2,2'-azobis[2-(2-imidazolin-2-yl)propane] disulfate dihydrate (VA-046B manufactured by Wako Pure Chemical Industries, Ltd., 10 hour half-life temperature: 46° C.), 2,2'-azobis[2-(2-imidazolin-2-yl)propane] (VA-061 manufactured by Wako Pure Chemical Industries, Ltd., 10 hour half-life temperature: 61° C.), 2,2'-azobis(2-amidinopropane) dihydrochloride (V-50 manufactured by Wako Pure Chemical Industries, Ltd., 10 hour half-life temperature: 56° C.), peroxodisulfuric acid and t-butyl hydroperoxide.

In light of solubility in water, ion balance and interaction with the monomers, it is preferable that the initiator be selected from 2,2'-azobis[2-methyl-N-(2-hydroxyethyl)propionamide], 2,2'-azobis(N-(2-carboxyethyl)-2-methylpropionamidine) n-hydrate, 4,4'-azobis(4-cyanopentanoic acid), 2,2'-azobis[2-(2-imidazolin-2-yl)propane] dihydrochloride, 2,2'-azobis[2-(2-imidazolin-2-yl)propane] disulfate dihydrate, 2,2'-azobis[2-(2-imidazolin-2-yl)propane], 2,2'-azobis(2-amidinopropane) dihydrochloride and peroxodisulfuric acid.

In light of solubility in organic solvents, ion balance and interaction with the monomers, it is preferable to use 2,2'-azobis(2,4-dimethylvaleronitrile) or 2,2'-azobis(isobutyronitrile).

The polymerization initiator may be added in an amount of 0.05 mass % to 10 mass % relative to the total weight of the monomers used in the polymerization.

The polymerization reaction may be performed in such a manner that the reaction vessel is heated to 50° C. to 200° C. in an oil bath or the like, and stirring is performed for 1 hour to 48 hours, or more preferably the reaction vessel is heated to 80° C. to 150° C., and stirring is performed for 5 hours to 30 hours. Under such reaction conditions, the copolymer of the invention can be obtained. The reaction atmosphere is preferably a nitrogen atmosphere.

Regarding the reaction procedure, all the raw materials may be added to the reaction solvent at room temperature and may be thereafter polymerized while performing heating at the above temperature. Alternatively, a mixture of the raw materials may be added at once or dropwise in small portions to the solvent that has been heated.

When the latter reaction procedure is adopted, the copolymer of the present invention may be prepared by a production method which includes a step in which a mixture including the compounds of the above-described formulae (A), (B) and optionally (C), a solvent and a polymerization initiator is added dropwise to a solvent kept at a temperature higher than the 10 hour half-life temperature of the polymerization initiator, and the compounds are reacted (polymerized).

The molecular weight of the copolymer in the present invention may be about several thousand to several million, preferably 5,000 to 5,000,000, more preferably 10,000 to 2,000,000, and most preferably 5,000 to 1,000,000. The copolymer may be a random copolymer, a block copolymer or a graft copolymer. The copolymerization reaction for producing the copolymer is not limited, and a known synthesis process performed in a solution such as polymerization utilizing radical polymerization, ion polymerization, photopolymerization or emulsion polymerization may be used. The copolymers according to the present invention may be used singly in accordance with the purpose, or a plurality of copolymers may be mixed in a ratio which may be changed appropriately in accordance with the purpose.

The coating agent used to form the coating in the cryopreservation vessel of the present invention may be prepared by diluting the desired copolymer to a predetermined concentration with a desired solvent as required.

Examples of the solvents include water, phosphate buffered saline (PBS) and alcohols. Examples of the alcohols include $C_{2-6}$ alcohols such as ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol. The solvents may be used singly, or may be combined into a mixed solvent. From the point of view of the dissolution of the copolymer, it is preferable that the solvent be selected from water, PBS, ethanol, propanol, and mixed solvents thereof, and more preferably selected from water, ethanol, and a mixed solvent thereof.

The coating agent may be prepared from a varnish containing the copolymer. The varnish containing the copolymer may be prepared by, for example, a production method which includes a step in which the compounds represented by the formulae (A), (B) and optionally (C) are reacted (polymerized) in a solvent at a total concentration of the compounds of 0.01 mass % to 20 mass %.

To form the coating film uniformly, the solid concentration in the coating agent is preferably 0.01 to 50 mass %. The concentration of the copolymer in the coating agent is preferably 0.01 to 4 mass %, more preferably 0.01 to 3 mass %, particularly preferably 0.01 to 2 mass %, and further preferably 0.01 to 1 mass %. If the concentration of the copolymer is below 0.01 mass %, the coating agent is too low in copolymer concentration and fails to form a coating film with a sufficient film thickness. If the concentration is above 4 mass %, the storage stability of the coating agent is deteriorated and there is a risk that the solutes may be precipitated or the coating agent may be gelled.

In addition to the copolymer and the solvent, the coating agent may include other materials as required without impairing the performance of the coating films that are obtained. Examples of such additional materials include preservatives, surfactants, primers for enhancing the fixing to the substrate, antifungal agents and sugars.

To control the ion balance of the copolymer in the coating agent, a step may be added in which the pH of the coating agent is adjusted beforehand. The pH may be adjusted by, for example, adding a pH adjuster to a composition including the copolymer and a solvent to control the pH of the composition to 3.5 to 8.5, or more preferably 4.0 to 8.0. The type and amount of the pH adjuster may be selected appropriately in accordance with factors such as the concentration of the copolymer and the ratio of anions and cations.

Examples of the pH adjusters include organic amines such as ammonia, diethanolamine, pyridine, N-methyl-D-glucamine and tris(hydroxymethyl)aminomethane; alkali metal hydroxides such as potassium hydroxide and sodium hydroxide; alkali metal halides such as potassium chloride and sodium chloride; inorganic acids such as sulfuric acid, phosphoric acid, hydrochloric acid and carbonic acid, and alkali metal salts thereof; quaternary ammonium cations such as choline; and mixtures thereof (for example, buffers such as phosphate buffered physiological saline). Of these, ammonia, diethanolamine, sodium hydroxide, choline, N-methyl-D-glucamine and tris(hydroxymethyl)aminomethane are preferable, and ammonia, diethanolamine, sodium hydroxide and choline are particularly preferable.

The cryopreservation vessel of the invention has, on at least a portion of the surface thereof, a coating formed from the coating agent described above. Specifically, the cryopreservation vessel has such a coating on at least a portion of the inner surface and/or the outer surface of the vessel which can be brought into contact with a suspension or solution containing cells or proteins.

The cryopreservation vessel may be a container that is usually used for the preservation of cells or proteins, such as a bottle, a tube, a vial, a plate or an ampoule.

Examples of the materials of the vessels include glass, metals, metal-containing compounds, semimetal-containing compounds, active carbon and resins. Examples of the metals include typical metals: (alkali metals: Li, Na, K, Rb, Cs; alkaline earth metals: Ca, Sr, Ba, Ra), magnesium group elements: Be, Mg, Zn, Cd, Hg; aluminum group elements: Al, Ga, In; rare earth elements: Y, La, Ce, Pr, Nd, Sm, Eu; tin group elements: Ti, Zr, Sn, Hf, Pb, Th; iron group elements: Fe, Co, Ni; earth-acid elements: V, Nb, Ta, chromium group elements: Cr, Mo, W, U; manganese group elements: Mn, Re; noble metals: Cu, Ag, Au; and platinum group elements: Ru, Rh, Pd, Os, Ir, Pt. Examples of the metal-containing compounds and the semimetal-containing compounds include ceramics which are basically metal oxides in the solid form sintered by heat treatment at a high temperature, semiconductors such as silicon, inorganic solid materials such as shaped products of inorganic compounds such as metal oxides or semimetal oxides (for example, silicon oxide and alumina), metal carbides or semimetal carbides, metal nitrides or semimetal nitrides (for example, silicon nitride), and metal borides or semimetal borides, aluminum, nickel-titanium, and stainless steel (for example, SUS304, SUS316 and SUS316L).

The resins may be natural resins or derivatives thereof, or synthetic resins. Some preferred natural resins and derivatives thereof are cellulose, cellulose triacetate (CTA), nitrocellulose (NC) and dextran sulfate immobilized celluloses. Some preferred synthetic resins are polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester, polypropylene (PP), polyvinylidene fluoride (PVDF), polyethersulfone (PES), polycarbonate (PC), polyvinyl chloride (PVC), polytetrafluoroethylene (PTFE), ultrahigh molecular weight polyethylene (UHPE), polydimethylsiloxane (PDMS), acrylonitrile-butadiene-styrene resin (ABS) and Teflon (registered trademark).

The vessel may be composed of a single material or a combination of two or more materials. Of the materials mentioned above, glass, silicon, silicon oxide, polystyrene (PS), polypropylene (PP), polyethersulfone (PES), polyethylene terephthalate (PET), polycarbonate (PC), polyvinyl chloride (PVC), Teflon (registered trademark), cycloolefin polymer (COP), polydimethylsiloxane (PDMS), or stainless steel (such as SUS304, SUS316 or SUS316L), or a combination of materials selected from above is preferable. Glass, polystyrene (PS), polypropylene (PP), or stainless steel (such as SUS304, SUS316 or SUS316L) is particularly preferable.

Another aspect of the invention resides in a method for producing a cryopreservation vessel having a coating on at least a portion of the surface of the vessel, the method including a step of bringing the above-described coating agent into contact with at least a portion of the surface of the vessel. The coating agent may be brought into contact with the surface of the vessel in any manner without limitation. For example, the vessel may be dipped into the coating agent; the coating agent may be added to the vessel and allowed to stand for a predetermined time; or the coating agent may be applied onto the surface of the vessel. Preferably, the contact is made by adding the coating agent to the vessel and allowing it to stand for a predetermined time. For example, the coating agent in a volume 0.5 to 1 time the total volume of the vessel may be added with use of a syringe or the like. The amount of time and temperature for the standing may be selected appropriately in accordance with the material of the vessel and the type of the coating agent. For example, the standing is performed at 10 to 35° C., preferably 20 to 30° C., or most preferably 25° C., for 5 minutes to 24 hours, or preferably 30 minutes to 3 hours. In the manner described above, a cryopreservation vessel can be produced which has a coating on at least a portion, or preferably over the entirety, of the surface of the vessel.

After the coating is formed on the surface of the vessel by the above method, specifically, after the coating is formed by the step in which the coating agent is brought into contact with at least a portion of the surface of the vessel, or preferably by the step in which the coating agent is added and allowed to stand for a predetermined time, the cryopreservation vessel may be subjected to actual use directly without a drying step or after being washed with water or a solvent in a sample that will be cryopreserved (such as, for example, water, buffered solution or medium).

More specifically, the cryopreservation vessel may be subjected to actual use directly without a drying step or after being washed with water or a solvent in a sample that will be cryopreserved (such as, for example, water, buffered solution or medium, particularly preferably medium (for example, DMEM (Dulbecco's modified eagle's medium)), within 48 hours, preferably within 24 hours, more preferably within 12 hours, still more preferably within 6 hours, even more preferably within 3 hours, or further preferably within 1 hour after the step in which the coating agent is brought into contact with at least a portion of the surface of the vessel, or preferably after the step in which the coating agent is added and allowed to stand for a predetermined time.

The vessel may be subjected to a drying step. The drying step is carried out under atmospheric pressure or under vacuum, preferably at a temperature in the range of −200° C. to 200° C. The drying step removes the solvent in the coating agent, and causes the copolymer of the invention to form ion bonds between the formula (a) and the formula (b), resulting in complete fixing to the base.

The coating may be formed by drying at, for example, room temperature (10° C. to 35° C., preferably 20° C. to 30° C., for example, 25° C.). To promote the formation of the coating, drying may be performed at, for example, 40° C. to 50° C. The drying step may be performed by a freeze drying method at a very low or low temperature (about −200° C. to −30° C.). Freeze drying is also called vacuum freeze drying, and is usually performed by freezing a wet product with a refrigerant and removing the solvent by sublimation under vacuum. Some example refrigerants generally used in the freeze drying are a mixed medium of dry ice and methanol (−78° C.), and liquid nitrogen (−196° C.).

If the drying temperature is below −200° C., a special refrigerant is needed and the treatment lacks versatility, and also such drying takes a long time for the sublimation of the solvent and thus is not efficient. If the drying temperature is above 200° C., the ion bonding reaction on the coating surface proceeds too far, and the surface loses hydrophilicity and comes to exhibit no resistance to the adhesion of cells or proteins. The drying temperature is more preferably 10° C. to 180° C., and still more preferably 25° C. to 150° C.

The coating of the present invention is produced through the simple steps described hereinabove. An irradiation step such as one described in Patent Literature 3 is not necessary.

To remove undesired components such as impurities and unreacted monomers remaining in the coating, and to adjust the ion balance of the copolymer in the coating, a step may be performed in which the coating film is washed with at least one solvent selected from water and aqueous electrolyte solutions. For example, the washing is preferably performed under running or ultrasonication of the solvent. The water and the aqueous electrolyte solutions may be heated beforehand in the range of, for example, 40° C. to 95° C. Some preferred aqueous electrolyte solutions are PBS, physiological saline (containing only sodium chloride), Dulbecco's phosphate buffered physiological saline, Tris buffered physiological saline, HEPES buffered physiological saline and Veronal buffered physiological saline, with PBS being particularly preferable. After being formed, the coating film remains strongly adhering to the base without leaching even when washed with water, PBS, alcohol or the like. Even when cells or proteins have become adhered to the coating, the film can be easily cleaned by water washing or the like and the surface of the vessel having the coating of the invention exhibits resistance to the adhesion of cells or proteins.

The film thickness of the coating formed on the surface of the vessel of the invention may be controlled appropriately in accordance with factors such as the shape of the vessel and the type of the sample, and may be substantially uniform over the entirety of the surface of the vessel or may be partly nonuniform. The film thickness is not particularly limited, but is preferably 10 to 1000 Å, more preferably 10 to 500 Å, and most preferably 10 to 300 Å.

The phrase "the coating has a resistance to a cryoprotectant" means that the thickness loss of the coating determined by the chemical resistance thickness test in ⟨Test Example 1⟩ described in Examples is not more than 50%, preferably not more than 35%, and most preferably not more than 20%.

The cryoprotectant is selected from the group consisting of ethylene glycol, propanediol, methanol, ethanol, dimethylacetamide, glycerol, polyethylene glycol, polyvinylpyrrolidone, hydroxyethyl starch, dextran, albumin, acetamide, acrylamide, propionamide, methacrylamide, isobutyramide, lactamide, nicotinamide, isophthalamide, acetonitrile, acetone and dimethyl sulfoxide. Of these, methanol, ethanol, acetonitrile, acetone and dimethyl sulfoxide are preferable, and methanol, acetonitrile, acetone and dimethyl sulfoxide are particularly preferable.

To a preservative liquid in which cells or proteins are preserved, the cryoprotectant is usually added in a concentration of 1 mass % to 100 mass %, preferably 2 mass % to 50 mass %, and most preferably 5 mass % to 20 mass %. The concentration is particularly preferably 5 mass % to 10 mass % in the case of cells, and 10 mass % to 20 mass % in the case of proteins.

EXAMPLES

Hereinbelow, the present invention will be described in greater detail based on discussions such as Synthetic Examples; Examples and Test Examples. However, it should be construed that the scope of the invention is not limited thereto.

The weight average molecular weight of copolymers shown in Synthetic Examples below is the results measured by gel filtration chromatography (hereinafter, abbreviated as GFC) or gel permeation chromatography (hereinafter, abbreviated as GPC). The details such as measurement conditions are described below.

(GFC Measurement Conditions)
Device: Prominence (manufactured by Shimadzu Corporation)
GFC columns: TSKgel GMPWXL (7.8 mm I.D.×30 cm)×2 to 3 columns
Flow rate: 1.0 mL/min
Eluent: aqueous ionic material solution or mixture thereof with EtOH
Column temperature: 40° C.
Detector: RI
Injection concentration: 0.05-0.5 mass % polymer solid
Injection volume: 100 μL
Calibration curve: third-order approximation curve
Standard samples: ten variations of polyethylene oxide (manufactured by Agilent Technologies Japan, Ltd.)
(GPC Measurement Conditions)
Device: HLC-8220 (manufactured by TOSOH CORPORATION)
GPC columns: Shodex (registered trademark)•Asahipak (registered trademark) (manufactured by SHOWA DENKO K.K.)×3 columns
Flow rate: 0.6 mL/min
Eluent: N,N-dimethylformamide (DMF)
Column temperature: 40° C.
Detector: RI
Injection concentration: 0.05-0.5 mass % polymer solid
Injection volume: 100 μL
Calibration curve: third-order approximation curve
Standard samples: ten variations of polystyrene (manufactured by TOSOH CORPORATION)

(Provision of Silicon Wafers)
Commercial silicon wafers for semiconductor evaluation were used directly.
(Preparation of QCM Sensors (PS))
A Au-deposited quartz crystal oscillator (Q-Sense, QSX304) was cleaned for 10 minutes using a UV/ozone cleaning device (UV253E, manufactured by Filgen, Inc.). Immediately thereafter, it was immersed into a solution of 0.0772 g of 2-aminoethanethiol (manufactured by Tokyo Chemical Industry Co., Ltd.) in 1000 mL of ethanol for 24 hours. The surface of the sensor was washed with ethanol and was allowed to dry naturally. The film sensor side was spin coated with a varnish obtained by dissolving 1.00 g of polystyrene (manufactured by Aldrich Corporation) in 99.00 g of toluene by use of a spin coater at 3500 rpm for 30 seconds, and the coating was dried at 120° C. for 1 minute. A QCM sensor (PS) was thus obtained.

⟨Synthetic Example 1⟩

While keeping the temperature at 60° C., 28.00 g of acid phosphoxyethyl methacrylate (product name: Phosmer M manufactured by Uni-Chemical Co., nonvolatile content measured by drying process at 100° C. for 1 hour: 91.8%, mixture of acid phosphoxyethyl methacrylate (44.2 mass %), bis[2-(methacryloyloxy)ethyl]phosphate (28.6 mass %) and others (27.2 mass %)) was stirred, and 21.37 g of 2-(dimethylamino)ethyl methacrylate was added thereto dropwise. While keeping the temperature at not more than 20° C., 133.96 g of pure water, then 44.65 g of ethanol and 0.25 g of 2,2'-azobis[N-(2-carboxyethyl)-2-methylpropionamidine] n-hydrate (VA-057 manufactured by Wako Pure Chemical Industries, Ltd.) were added to the mixture sequentially. The resultant mixture was sufficiently stirred to uniformity. The mixture liquid thus obtained which contained the above materials was introduced into a dropping funnel. Separately, 267.93 g of pure water was added to a three-necked flask having a cooling tube. While flowing nitrogen into the flask and while performing stirring, the temperature was increased to reflux temperature. While maintaining this state, the dropping funnel containing the mixture liquid was fitted to the three-necked flask, and the mixture liquid was dropped to the boiling mixture of pure water and ethanol over a period of 2 hours. After the completion of the dropwise addition, the system was heated and stirred for 24 hours while maintaining the above environment. Consequently, 496.16 g of a copolymer-containing varnish having a solid content of about 9.70 mass % was obtained. The GFC analysis of the transparent liquid obtained showed that the weight average molecular weight was about 280,000.

⟨Synthetic Example 2⟩

29.95 g of choline (48-50% aqueous solution manufactured by Tokyo Chemical Industry Co., Ltd.) was added to 25.00 g of acid phosphoxyethyl methacrylate (product name: Phosmer M manufactured by Uni-Chemical Co., nonvolatile content measured by drying process at 100° C. for 1 hour: 91.8%, mixture of acid phosphoxyethyl methacrylate (44.2 mass %), bis[2-(methacryloyloxy)ethyl]phosphate (28.6 mass %) and others (27.2 mass %)) while performing cooling so that the temperature was 35° C. or below. The resultant mixture was stirred to uniformity. While keeping the temperature at not more than 35° C., 20.95 g of an 80% aqueous methacroylcholine chloride solution (manufactured by Tokyo Chemical Industry Co., Ltd.), 28.67 g of butyl methacrylate (manufactured by Tokyo Chemical Industry Co., Ltd.), 0.70 g of 2,2'-azobis(2,4-dimethylvaleronitrile) (V-65 manufactured by Wako Pure Chemical Industries, Ltd.) and 110.84 g of ethanol were added to the mixture liquid sequentially. Further, an aqueous solution of 0.70 g of 2,2'-azobis[N-(2-carboxyethyl)-2-methylpropionamidine] n-hydrate (VA-057 manufactured by Wako Pure Chemical Industries, Ltd.) in 27.71 g of pure water was added to the solution while keeping the temperature at not more than 35° C. The resultant mixture was sufficiently stirred to uniformity. The mixture liquid thus obtained which contained the above materials was introduced into a dropping funnel. Separately, 56.81 g of pure water and 131.62 g of ethanol were added to a three-necked flask having a cooling tube. While flowing nitrogen into the flask and while performing stirring, the temperature was increased to reflux temperature. While maintaining this state, the dropping funnel containing the mixture liquid was fitted to the three-necked flask, and the mixture liquid was dropped to the boiling mixture of pure water and ethanol over a period of 1 hour. After the completion of the dropwise addition, the system was heated and stirred for 24 hours while maintaining the above environment. After 24 hours, the system was cooled. Consequently, 432.97 g of a copolymer-containing varnish having a solid content of about 19.86 mass % was obtained. The GPC analysis of the colloidal liquid obtained showed that the weight average molecular weight was about 8,500.

⟨Preparation Example 1⟩

31.5 g of pure water, 1.35 g of ethanol, and 0.24 g of a 1 mol/L aqueous sodium hydroxide solution (1 N) (manufactured by KANTO CHEMICAL CO., INC.) were added to 5.00 g of the copolymer-containing varnish obtained in Synthetic Example 1. The mixture was sufficiently stirred to give a coating agent. The pH was 7.3. The silicon wafer was dipped into the coating agent and was dried in an oven at 45° C. for 24 hours. Thereafter, the wafer was sufficiently washed with PBS and pure water. Thus, a coating film was formed on the silicon wafer. The film thickness of the coating film on the silicon wafer was measured with an optical interferometric thickness gauge to be 105 Å.

Separately, the QCM sensor (PS) was spin coated with the coating agent at 3500 rpm for 30 seconds and was subjected to a drying step in which the film was baked in an oven at 45° C. for 24 hours. Thereafter, the sensor was washed two times with each of PBS and ultrapure water. A surface-treated QCM sensor (PS) was thus obtained.

Separately, a SUS316L QCM sensor (manufactured by MEIWAFOSIS CO., LTD.) which had been plasma cleaned was spin coated with the coating agent at 3500 rpm for 30 seconds and was subjected to a drying step in which the film was baked in an oven at 50° C. for 24 hours. Thereafter, the sensor was washed two times with each of PBS and ultrapure water. A surface-treated QCM sensor (SUS316L) was thus obtained.

⟨Preparation Example 2⟩

1.19 g of 1 mol/L hydrochloric acid (1 N) (manufactured by KANTO CHEMICAL CO., INC.), 26.78 g of pure water, and 62.54 g of ethanol were added to 10.00 g of the copolymer-containing varnish obtained in Synthetic Example 2. The mixture was sufficiently stirred to give a coating agent. The pH was 3.5. A coated silicon wafer and surface-treated QCM sensors (PS and SUS316L) were obtained in the same manner as in Preparation Example 1. The film thickness of the coating film on the silicon wafer was measured with an optical interferometric thickness gauge to be 451 Å.

⟨Test Example 1⟩
(Chemical Resistance Thickness Test)

The silicon wafers coated in Preparation Examples were immersed in pure water, 50% aqueous acetonitrile solution (abbreviated as ACN 50%), acetonitrile (abbreviated as ACN 100%), and 20% aqueous dimethyl sulfoxide solution (abbreviated as DMSO 20%) at 25° C. for 24 hours. The silicon wafers were then washed with pure water and dried on a hot plate at 50° C. for 1 minute. The film thicknesses of the coating films were measured again with an optical interferometric thickness gauge, the results being described in Table 1 below.

TABLE 1

|  | Without treatment | Pure water | ACN50% | ACN100% | DMSO20% |
|---|---|---|---|---|---|
| Preparation Example1 | 105 | 105 | 71 | 103 | 91 |
| Preparation Example2 | 451 | 451 | — | — | 523 |

* The unit is Å.

The wafers from Preparation Example 1 were demonstrated to have substantially no change in film thickness before and after the chemical soaking, except in the 50% aqueous acetonitrile solution. The wafers from Preparation Example 2 exhibited chemical resistance to DMSO 20%, there being no thickness loss.

⟨Test Example 2⟩
(Chemical Resistance Test with QCM-D: QCM Sensors (PS))

The surface-treated QCM sensors (PS) obtained in Preparation Examples were immersed in pure water, ACN 50%, ACN 100% and DMSO 20% for 24 hours. The sensors were then washed with pure water and dried on a hot plate at 50° C. for I minute. The sensors were each fitted to quartz crystal microbalance with dissipation monitoring QCM-D (E4, Q-Sense), and PBS was passed until a stable baseline was achieved in which the change in frequency in one hour was 1 Hz or less. Next, the frequency of the stable baseline was taken as 0 Hz and PBS was passed for about 10 minutes. Subsequently, a solution of 0.1 g of γ-globulin derived from human blood (Aldrich Corporation) in 1 L of PBS, was passed for about 30 minutes. Thereafter, PBS was passed again for about 20 minutes, and the adsorption induced shift in frequency (Δf) of the eleventh overtone was read. Using Q-Tools (Q-Sense), the adsorption induced frequency shift (Δf) was analyzed based on the Sauerbrey equation which explains the conversion of the adsorption induced frequency shift (Δf) to the mass change per unit area (ng/cm$^2$), the results being shown in Table 2 below as the amounts of protein adhesion. An untreated PS sensor was used as Comparative Example.

TABLE 2

|  | Without treatment | Pure water | ACN50% | ACN100% | DMSO20% |
|---|---|---|---|---|---|
| Preparation Example1 | 1144 | 204 | 657 | 402 | 194 |
| Preparation Example2 | 1144 | 9 | 8 | 62 | 1 |

* The unit is ng/cm$^2$

The treated sensors were demonstrated to resist protein adhesion as compared to the untreated sensor regardless of the types of solvents. The sensors from Preparation Example 2 attained protein adhesion inhibitory effects one or two orders of magnitude higher than those in Preparation Example 1.

⟨Test Example 3⟩
(Chemical Resistance Test with QCM-D: QCM Sensors (SUS316L))

The surface-treated sensors obtained in Preparation Examples were each fitted to quartz crystal microbalance with dissipation monitoring QCM-D (E4, Q-Sense), and PBS was passed until a stable baseline was achieved in which the change in frequency in one hour was 1 Hz or less. Next, the frequency of the stable baseline was taken as 0 Hz and PBS was passed for about 10 minutes. Subsequently, a solution of 0.1 g of γ-globulin derived from human blood (Aldrich Corporation) in 1 L of PBS, was passed for about 30 minutes. Thereafter, PBS was passed again for about 20 minutes, and the adsorption induced shift in frequency ($\Delta f$) of the eleventh overtone was read. Using Q-Tools (Q-Sense), the adsorption induced frequency shift ($\Delta f$) was analyzed based on the Sauerbrey equation which explains the conversion of the adsorption induced frequency shift ($\Delta f$) to the mass change per unit area (ng/cm$^2$), the results being shown in Table 3 below as the amounts of protein adhesion. An untreated SUS316L sensor was used as Comparative Example.

TABLE 3

| | No treatment | Preparation Example 1 | Preparation Example 2 |
|---|---|---|---|
| Amount of protein adhesion (ng/cm$^2$) | 178 | 1 | 0 |

⟨Example 1⟩
1.19 g of 1 mol/L hydrochloric acid (1 N) (manufactured by KANTO CHEMICAL CO., INC.), 26.78 g of pure water, and 62.54 g of ethanol were added to 10.00 g of the copolymer varnish obtained in Synthetic Example 2. The mixture was sufficiently stirred to give a coating agent. The pH was 3.5. Microtubes 1.5 mL (manufactured by Quality Scientific Plastics, material: polypropylene (PP)) were each loaded with 1.5 mL of the coating agent and were allowed to stand at 25° C. for 1 hour. The coating agent was removed, and the tubes were dried at 25° C. for 18 hours. Thereafter, the tubes were washed sufficiently with pure water. Coated microtubes were thus obtained.

⟨Test Example 4⟩
(Organic Solvent Resistance Evaluation)

[Organic solvent treatment] DMSO and ACN were each diluted with pure water to 10% and 50%. Similarly, acetone (abbreviated as ACT), methanol (abbreviated as MeOH) and ethanol (abbreviated as EtOH) ere each diluted with pure water to 10% and 50%. The diluted solvents, pure water, 100% DMSO and 100% ACN, each 1.5 mL, were added to the coated tubes and uncoated tubes described in Example 1, and PROTEOSAVE (registered trademark) SS 1.5 mL Microtubes (MS-4215M, Comparative Example) manufactured by Sumitomo Bakelite Co., Ltd. The tubes were allowed to stand at room temperature for 5 hours, and the organic solvents were removed. The tubes were washed sufficiently with pure water and dried at room temperature.

[Evaluation of Organic Solvent Resistance by Measurement of Amount of Protein Adhesion]

Horseradish peroxidase (abbreviated as HRP) labeled Goat Anti-Mouse IgG (available from SoutherBioteck) was diluted with phosphate buffered physiological saline, and was added to the coated tubes, uncoated tubes and comparative example tubes that had been treated with the organic solvents above. The tubes were allowed to stand at room temperature for 30 minutes, and were washed with phosphate buffered physiological saline. Thereafter, TMB 1-Component Microwell Peroxidase Substrate, SureBlue (available from Kirkegaard & Perry Laboratories, Inc., abbreviated as TMB) was added and reacted with HRP. The reaction was terminated by the addition of TMB Stop Solution (available from Kirkegaard & Perry Laboratories, Inc.). The optical density (450 nm) of this TMB solution was measured with a plate reader (SPECTRAMAX 190, Molecular Devices), and was evaluated as the amount of protein adhesion. The results are described in FIGS. 1 to 5.

As shown in FIGS. 1 to 5, the coated tubes were demonstrated to be more resistant to protein adhesion than the uncoated tubes even after treated with organic solvents. The coated tubes compared equally or favorably to the comparative example tubes in terms of protein adhesion inhibitory performance, and therefore their resistance to organic solvents was probably equal to or higher than that of the comparative example tubes. In particular, the coated tubes exhibited higher resistance to DMSO, a conventional cryoprotectant, than the comparative example tubes.

⟨Example 2⟩
1.19 g of 1 mol/L hydrochloric acid (1 N) (manufactured by KANTO CHEMICAL CO., INC.), 26.78 g of pure water, and 62.54 g of ethanol were added to 10.00 g of the copolymer varnish obtained in Synthetic Example 2. The mixture was sufficiently stirred to give a coating agent. The pH was 3.5. Microtubes 1.5 mL (manufactured by Quality Scientific Plastics, material: polypropylene (PP)) were each loaded with 1.5 mL of the coating agent and were allowed to stand at 25° C. for 1 hour. The coating agent was removed, and the tubes were dried at 25° C. for 18 hours. Thereafter, the tubes were washed sufficiently with pure water. Coated microtubes were thus obtained.

⟨Test Example 5⟩
(Protein Storage Test)

10% DMSO was prepared using aqueous phosphate buffered solution. Subsequently, FLUORESCEIN-5-isothiocyanate-labeled bovine serum albumin (abbreviated as FITC-BSA) was diluted with the above dilute solvent. The protein solution was added to the coated tubes and uncoated tubes described in Example 2 and was stored at −80° C. for 1 week. The portions of the protein solution recovered from the tubes were analyzed with a plate reader (Enspire, PerkinElmer) (Ex. 494 nm, Em. 521 nm) to determine the fluorescence intensity. The amounts of recovered protein were thus estimated. The results are shown in FIG. 6.

Figure 6:
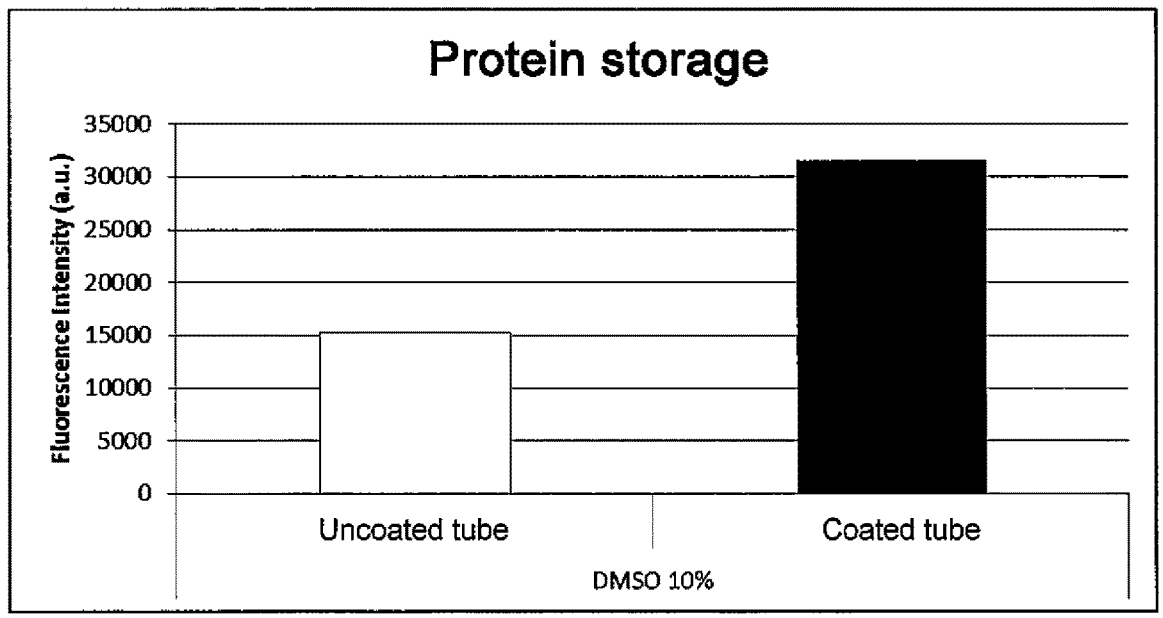
FIG. 6 is a graph which shows the results of measurement of the amounts of protein recovered from a coated tube of Example 2 and an uncoated tube in a protein storage test described in Test Example 5.

As shown in FIG. 6, the coated tubes allowed more protein to be recovered.

⟨Example 3⟩
1.19 g of I mol/L hydrochloric acid (1 N) (manufactured by KANTO CHEMICAL CO., INC.), 26.78 g of pure water, and 62.54 g of ethanol were added to 10.00 g of the copolymer varnish obtained in Synthetic Example 2. The mixture was sufficiently stirred to give a coating agent. The pH was 3.5. Cell storage vials (Cryogenic Vial, 2.0 mL, Thermo SCIENTIFIC, material: polypropylene) were each loaded with 2.0 mL of the coating agent and were allowed to stand at 25° C. for 1 hour. The coating agent was removed, and the vials were dried at 25° C. for 18 hours. Thereafter, the vials were washed sufficiently with pure water. Coated cell storage vials were thus obtained.

⟨Test Example 6⟩
(Cell Storage Test)

A cell culture medium was prepared by adding 10 (v/v) % DMSO and 10% Fetal Bovine Serum (CORNING) to Dulbecco's Modified Eagle Medium (manufactured by Wako Pure Chemical Industries, Ltd.). Mouse embryonic fibroblasts C3H10T1/2 (available from DS Pharma Biomedical Co., Ltd.) were added to the medium so that the cell concentration would be 1×10$^5$ cells/mL. The cell-containing culture, 1 mL, was added to the coated vials of Example 3. Thereafter, the vials were placed into BIO FREEZING VESSEL BICELL (registered trademark) (NIHON FREEZER CO., LTD.) and were stored in the freezer at −80° C. for 1 week. After the storage, the cell suspensions were melted in a water bath at 37° C. and were mixed with 0.4 (w/v) % Trypan Blue Solution (manufactured by Wako Pure Chemical Industries, Ltd.) in 1:1 ratio. The cell count was measured using TC20 (trademark) Automated Cell Counter (BIORAD). The results are shown in FIG. 7.

Figure 7:
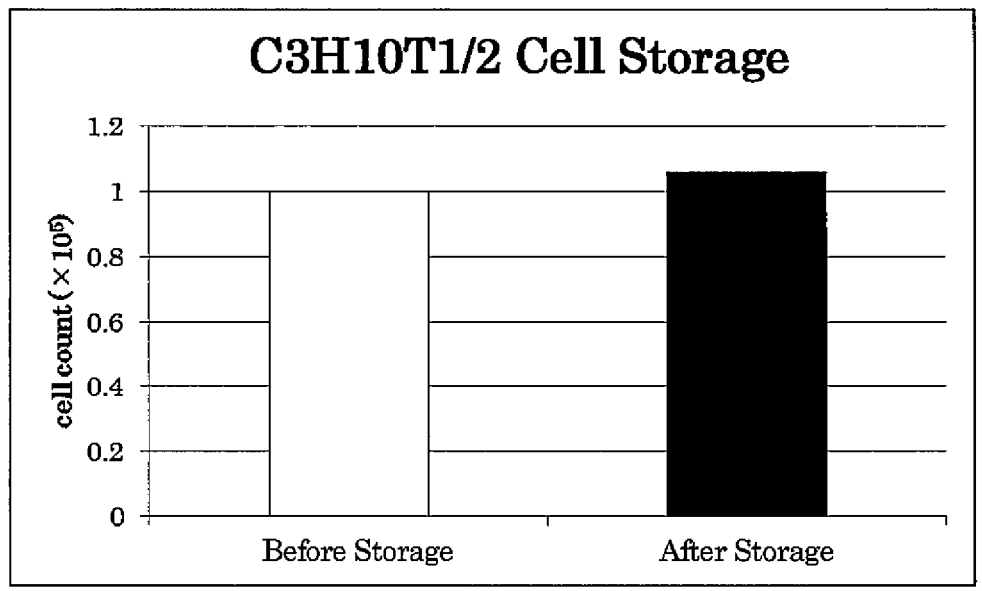
FIG. 7 is a graph which shows the results of measurement of cell counts in a coated vial of Example 3 before and after a cell storage test described in Test Example 6.

As shown in FIG. 7, the coated vials of Example 3 allowed the cells to be stored at −80° C. without causing a significant change in cell count before and after the storage. Thus, the test confirmed no major influence on cell storage.

⟨Example 4⟩

1.19 g of 1 mol/L hydrochloric acid (1 N) (manufactured by KANTO CHEMICAL CO., INC.), 26.78 g of pure water, and 62.54 g of ethanol were added to 10.00 g of the copolymer varnish obtained in Synthetic Example 2. The mixture was sufficiently stirred to give a coating agent. The pH was 3.5. The coating agent, 1.0 mL, was added to plasma-cleaned stainless steel storage vessels 50 mL (manufactured by AS ONE Corporation, material: SUS316), and was allowed to stand at 25° C. for 1 hour. In this manner, a coating was formed mainly on a bottom portion of the inner wall of the vessels. The coating agent was removed, and the vessels were subjected to a drying step in which the coating was baked in an oven at 50° C. for 24 hours. Thereafter, the vessels were washed sufficiently with pure water. Coated stainless steel storage vessels were thus obtained.

⟨Test Example 7⟩

[Evaluation of Amounts of Protein Adhesion to Stainless Steel Storage Vessels]

Figure 8:
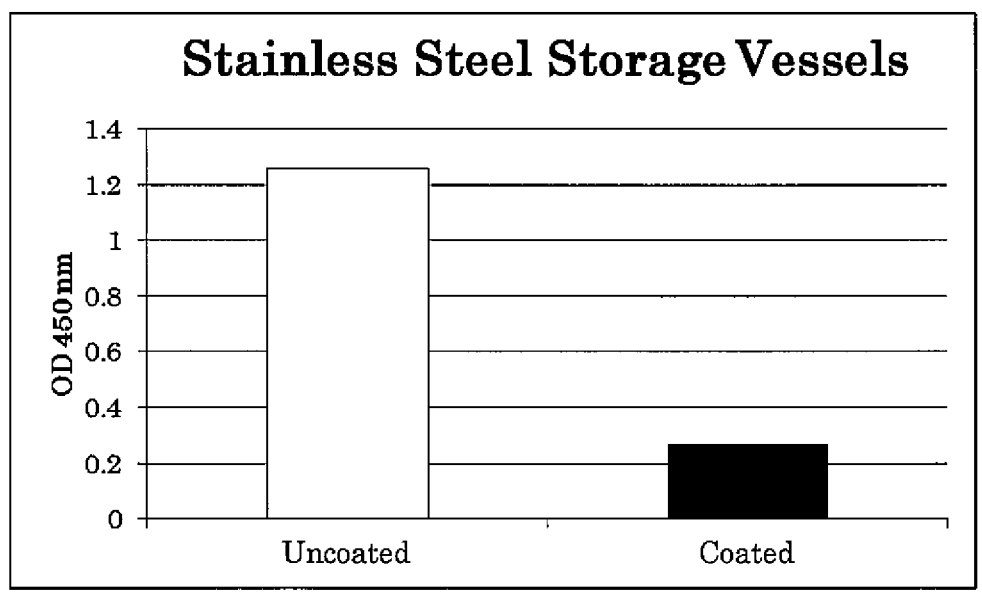
FIG. 8 is a graph which shows the results of evaluation of the amounts of protein adhesion to a coated stainless steel preservation vessel of Example 4 and an uncoated stainless steel preservation vessel in the test described in Test Example 7.

Horseradish peroxidase (abbreviated as HRP) labeled Goat Anti-Mouse IgG (available from SoutherBioteck) was diluted with phosphate buffered physiological saline, and was added to the coated stainless steel storage vessels and uncoated stainless steel storage vessels described above. The vessels were allowed to stand at room temperature for 30 minutes, and were washed with phosphate buffered physiological saline. Thereafter, TMB 1-Component Microwell Peroxidase Substrate, SureBlue (available from Kirkegaard & Perry Laboratories, Inc., abbreviated as TMB) was added and reacted with HRP. The reaction was terminated by the addition of TMB Stop Solution (available from Kirkegaard & Perry Laboratories, Inc.). The optical density (450 nm) of this TMB solution was measured with a plate reader (SPECTRAMAX 190, Molecular Devices), and was evaluated as the amount of protein adhesion. The results are described in FIG. 8.

The amount of protein adhesion was smaller in the coated storage vessels.

INDUSTRIAL APPLICABILITY

The cell or protein cryopreservation vessels of the present invention can contain a suspension or solution of cells or proteins without allowing the cells or proteins to adhere to the surface of the vessel (the surface which can be brought into contact with the suspension or solution of cells or proteins) during freezing, preservation and melting steps, thus making it possible to recover the cells or proteins from the suspension or solution efficiently. Further, the coating in the vessel of the invention can be firmly fixed to resins such as plastics, and can be easily formed on at least a portion of the surface of the vessel. Furthermore, the coating is highly resistant not only to aqueous solvents but also to organic solvents (for example, cryoprotectants, in particular, dimethyl sulfoxide), and is therefore stable and does not adversely affect the cells or proteins during the steps of freezing, preservation and melting of cells or proteins. Thus, the cell or protein cryopreservation vessels of the present invention can be used for the storage of a variety of cryopreservation solutions.

The invention claimed is:

1. A cell or protein cryopreservation vessel comprising a coating on at least a portion of the surface thereof, wherein the coating comprises a copolymer including a repeating unit containing a group represented by formula (a), a repeating unit containing a group represented by formula (b), and a repeating unit represented by formula (c1):

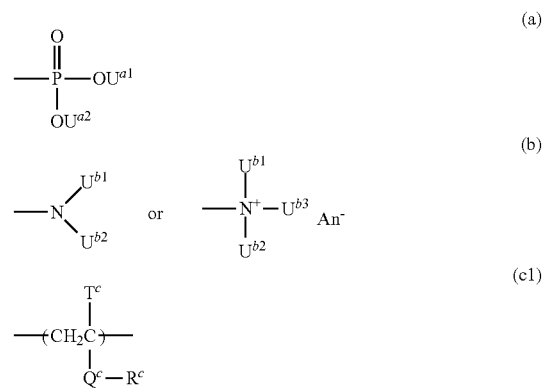

wherein $U^{a1}$, $U^{a2}$, $U^{b1}$, $U^{b2}$ and $U^{b3}$ are each independently a hydrogen atom or a $C_{1-5}$ linear or branched alkyl group, and An$^-$ is an anion selected from the group consisting of halide ion, inorganic acid ion, hydroxide ion and isothiocyanate ion, $T^c$ independently at each occurrence is a hydrogen atom or a $C_{1-5}$ linear or branched alkyl group;

$Q^c$ is a single bond, an ether bond or an ester bond; and $R^c$ is a $C_{1-18}$ linear or branched alkyl group, a $C_{3-10}$ cyclic hydrocarbon group, a $C_{6-10}$ aryl group, a $C_{7-15}$ aralkyl group or a $C_{7-15}$ aryloxyalkyl group, wherein the aryl moiety may be substituted with a $C_{1-5}$ linear or branched alkyl group which may be substituted with a halogen atom.

2. The vessel according to claim 1, wherein the copolymer includes repeating units represented by the following formulae (a1) and (b1):

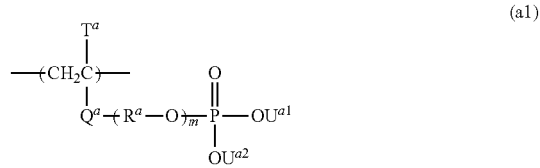

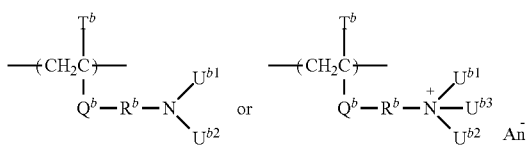

wherein $T^a$ and $T^b$ are each independently a hydrogen atom or a $C_{1-5}$ linear or branched alkyl group;

$Q^a$ and $Q^b$ are each independently a single bond, an ester bond or an amide bond;

$R^a$ and $R^b$ are each independently a $C_{1-10}$ linear or branched alkylene group which may be substituted with a halogen atom;

$U^{a1}$, $U^{a2}$, $U^{b1}$, $U^{b2}$ and $U^{b3}$ are each independently a hydrogen atom or a $C_{1-5}$ linear or branched alkyl group;

$An^-$ is an anion selected from the group consisting of halide ion, inorganic acid ion, hydroxide ion and isothiocyanate ion; and m is an integer of 0 to 6.

3. The vessel according to claim 2, wherein the coating has a resistance to a cryoprotectant.

4. The vessel according to claim 3, wherein the cryoprotectant is selected from the group consisting of ethylene glycol, propanediol, methanol, ethanol, dimethylacetamide, glycerol, polyethylene glycol, polyvinylpyrrolidone, hydroxyethyl starch, dextran, albumin, acetamide, acrylamide, propionamide, methacrylamide, isobutyramide, lactamide, nicotinamide, isophthalamide, acetonitrile, acetone and dimethyl sulfoxide.

5. The vessel according to claim 1, wherein the coating has a resistance to a cryoprotectant.

6. The vessel according to claim 5, wherein the cryoprotectant is selected from the group consisting of ethylene glycol, propanediol, methanol, ethanol, dimethylacetamide, glycerol, polyethylene glycol, polyvinylpyrrolidone, hydroxyethyl starch, dextran, albumin, acetamide, acrylamide, propionamide, methacrylamide, isobutyramide, lactamide, nicotinamide, isophthalamide, acetonitrile, acetone and dimethyl sulfoxide.

* * * * *